(12) United States Patent
Oh et al.

(10) Patent No.: US 10,605,764 B2
(45) Date of Patent: Mar. 31, 2020

(54) SOLID ELECTROLYTE CARBON DIOXIDE SENSOR AND MANUFACTURING METHOD THEREOF

(71) Applicants: Hyundai Motor Company, Seoul (KR); NANOIONICS KOREA CO., LTD., Gangneung-si (KR)

(72) Inventors: Sun-Mi Oh, Bucheon-si (KR); Hyun-Soo Sohn, Suwon-si (KR); Jong-Min Kwon, Gunpo-si (KR); Yang-Ki Kim, Seoul (KR); Tae-Won Lee, Seoul (KR); Ji-Hye Kim, Seoul (KR)

(73) Assignees: Hyundai Motor Company, Seoul (KR); NANOIONICS KOREA CO., LTD., Gangneung-si (KR)

( * ) Notice: Subject to any disclaimer, the term of this patent is extended or adjusted under 35 U.S.C. 154(b) by 152 days.

(21) Appl. No.: 15/365,724

(22) Filed: Nov. 30, 2016

(65) Prior Publication Data

US 2017/0356872 A1    Dec. 14, 2017

(30) Foreign Application Priority Data

Jun. 14, 2016 (KR) .................. 10-2016-0073506

(51) Int. Cl.
*G01N 27/407* (2006.01)
*C04B 37/00* (2006.01)
(Continued)

(52) U.S. Cl.
CPC ......... *G01N 27/4074* (2013.01); *B32B 37/06* (2013.01); *C04B 37/00* (2013.01);
(Continued)

(58) Field of Classification Search
CPC ............ G01N 27/4074; G01N 27/4076; C04B 37/00; B32B 37/06; B32B 37/02; B32B 2315/02; B32B 2457/00
See application file for complete search history.

(56) References Cited

U.S. PATENT DOCUMENTS 5,772,863 A * 6/1998 Shoemaker ........ G01N 27/4071
                                                    204/424
6,022,464 A * 2/2000 Schumann ......... G01N 27/4071
                                                    204/291
(Continued)

FOREIGN PATENT DOCUMENTS

JP    H09-133650 A  *  5/1997
JP      3017538 B2    12/1999
(Continued)

OTHER PUBLICATIONS

P.G. Bruce & A.R. West "Ionic Conductivity of LISICON solid solutions, Li2+2xZn1—xGeO4", Journal of Solid State Chemistry, 44(3): Abstract only, Oct. 1982.*

*Primary Examiner* — J. Christopher Ball
(74) *Attorney, Agent, or Firm* — Morgan, Lewis & Bockius LLP

(57) ABSTRACT

A solid electrolyte $CO_2$ sensor may include a solid electrolyte bonded to a substrate to join and seal the substrate, a sensing electrode formed at a first side of the solid electrolyte, and a reference electrode formed between a second side of the solid electrolyte and one surface of the substrate, and sealed by the solid electrolyte and the substrate.

18 Claims, 23 Drawing Sheets

(51) Int. Cl.
  *B32B 37/06* (2006.01)
  *B32B 37/02* (2006.01)
(52) U.S. Cl.
  CPC .......... *G01N 27/4076* (2013.01); *B32B 37/02* (2013.01); *B32B 2315/02* (2013.01); *B32B 2457/00* (2013.01)

(56) References Cited

U.S. PATENT DOCUMENTS

| | | | |
|---|---|---|---|
| 6,325,905 B1* | 12/2001 | Matsui | G01N 27/4071 204/424 |
| 2007/0138020 A1* | 6/2007 | Balagopal | C02F 1/4674 205/500 |
| 2011/0226042 A1* | 9/2011 | Yu | G01N 27/4074 73/31.05 |
| 2014/0308571 A1 | 10/2014 | Gaben et al. | |

FOREIGN PATENT DOCUMENTS

| | | |
|---|---|---|
| KR | 10-0305698 B1 | 12/2001 |
| KR | 10-2007-0095205 A | 9/2007 |
| KR | 10-2009-0097437 A | 9/2009 |
| KR | 10-2015-0073164 A | 6/2015 |
| KR | 10-2015-0124467 A | 11/2015 |

\* cited by examiner

SOLID ELECTROLYTE CARBON DIOXIDE SENSOR AND MANUFACTURING METHOD THEREOF

CROSS-REFERENCE TO RELATED APPLICATIONS

The present application claims priority to Korean Patent Application No. 10-2016-0073506, filed Jun. 14, 2016, the entire contents of which is incorporated herein for all purposes by this reference in its entirety.

BACKGROUND OF THE INVENTION

Field of the Invention

The present invention relates to a solid electrolyte $CO_2$ sensor and a manufacturing method thereof, and more particularly, to a solid electrolyte $CO_2$ sensor in which the joining and sealing of a reference electrode by a reaction caused by a heat treatment between a substrate and a solid electrolyte allows the reference electrode to suppress a side reaction such as adsorption of moisture, and a manufacturing method thereof.

Description of Related Art

Automobiles are a means of transportation, which is essential for human life, and make life richer and more convenient. Recently, automobiles have become more high-end, various options have been added, and among them, technologies for constructing a safe driving system of the automobile have been studied. As efforts to create a comfortable environment for safe driving during the driving have been accelerated, alternatives such as replacement of components applied to seats of vehicles with materials which emit less carcinogens have been suggested, and among them, interests in the quality of air inside the vehicle are increasing and much attention has been paid to carbon dioxide ($CO_2$). Carbon dioxide affects humans in a sealed space in various ways, is a factor affecting driving, and is responsible for reducing the driver's brain activities and causing drowsy driving. Accordingly, the real-time monitoring of the concentration of carbon dioxide for safe driving of vehicles and the function of monitoring and suppressing the environment for causing drowsy driving in real time in connection with the air conditioning system of vehicles in addition to that have drawn attention. Accordingly, there is a need for a sensor for measuring the concentration of carbon dioxide, and as a solution to the need, optical (non-dispersive infrared: NDIR) sensors, semiconductor-type gas sensors, and home or universal sensors in a solid electrolyte system have been suggested.

Meanwhile, carbon dioxide is a gas whose concentration is difficult to measure as a chemically very stable gas in the atmosphere, the optical sensor is most frequently used as a sensor for sensing the carbon dioxide, and this system is a system in which light with a specific wavelength of emitted laser is absorbed by carbon dioxide in the air, the amount of intensity of light reduced is sensed, and the amount of carbon dioxide is measured. This device has an advantage in that selectivity, sensitivity and reproducibility are excellent, but has problems in that a hermetically sealed space is required for measurement, and the volume is large and the weight is very heavy due to the physical sizes of constituent elements and filters. In particular, since the driving part and the measurement device are very expensive and the configuration of the processing part for control is complex, the price of the overall measurement equipment is definitely high, and accordingly, this device fails to be widely utilized even though the use thereof is very diverse.

As another system for measuring the concentration of carbon dioxide, a semiconductor-type gas sensor using a semiconductor compound such as $SnO_2$ or $TiO_2$ is used, and uses a principle of measuring the concentration of the gas through a change in resistance displayed when gas particles are adsorbed on the surface of the semiconductor compound. In this case, there is an advantage in that a sensor in the form of a thin film-type device can be manufactured, but there is also a disadvantage in that the gas selectivity significantly deteriorates because it is difficult to tell different gas particles to be adsorbed apart, and accordingly, it is difficult to use the semiconductor-type gas sensor as a device to select and measure only carbon dioxide.

The home or universal sensor in a solid electrolyte system in the related art has a limitation in use for an automobile because sensor signals are affected by reactive gases such as moisture, and the durability deteriorates. Therefore, there is a need for developing a solid electrolyte $CO_2$ sensor which may overcome the limitation of the universal sensor in a solid electrolyte system.

The above information disclosed in this Background section is only for enhancement of understanding of the background of the invention and therefore it may contain information that does not form the prior art that is already known in this country to a person of ordinary skill in the art.

BRIEF SUMMARY

Various aspects of the present invention are directed to providing a solid electrolyte $CO_2$ sensor which suppresses a side reaction of moisture due to the improvement in sealing performance, and monitors $CO_2$ in real time.

In addition, various aspects of the present invention are directed to providing a method for manufacturing a solid electrolyte $CO_2$ sensor by omitting the sealing in the manufacturing process to simplify the manufacturing system and reduce the manufacturing costs thereof.

According to various aspects of the present invention, a solid electrolyte $CO_2$ sensor may include a solid electrolyte bonded to a substrate to join and seal the substrate, a sensing electrode formed at a first side of the solid electrolyte, and a reference electrode formed between a second side of the solid electrolyte and one surface of the substrate, and sealed by the solid electrolyte and the substrate.

The reference electrode may include at least one of a two phase mixture of Li(Na)—Ti(Fe)—O systems and Pt(Au).

The sensing electrode may be selected from the group consisting of $A_2CO_3$ (A=Li, Na), and a mixture of $A_2CO_3$ (A=Li, Na) and $BCO_3$ (B=Ba, Ca, Sr).

The solid electrolyte may be $Na_{1+X}Zr_2Si_XP_{3-X}O_{12}$ and $0<X<3$.

The solid electrolyte may be $Li_{2+2X}Zn_{1-X}GeO_4$, and $0<X<1$.

An area of a solid electrolyte which is bonded to the substrate and does not join and seal the substrate may be 20 to 90% of an area of the entire solid electrolyte.

The substrate may include alumina or mullite.

According to various aspects of the present invention, a method for manufacturing a solid electrolyte $CO_2$ sensor may include stacking a reference electrode on a substrate, stacking a solid electrolyte having a larger area than the reference electrode stacked on the substrate to stack an end portion of the solid electrolyte on the substrate, a first heat treatment, of subjecting the substrate, the reference electrode, and the solid electrolyte which are stacked to heat treatment to join and seal the substrate, the reference electrode, and the solid electrolyte, stacking a sensing electrode on the stacked solid electrolyte, and a second heat treatment, of performing a heat treatment in order to bond the sensing electrode onto the solid electrolyte.

The reference electrode may include at least one of a two phase mixture of Li(Na)—Ti(Fe)—O systems and Pt(Au).

The solid electrolyte may have a thickness of 200 to 400 μm.

In the stacking of the solid electrolyte, an area of a solid electrolyte which is bonded to the substrate and does not join and seal the substrate may be 20 to 90% of an area of the entire solid electrolyte.

In the stacking of the solid electrolyte, a sintered body or a green sheet may be used.

When the first heat treatment uses a sintered body in the stacking of the solid electrolyte, a heat treatment for joining and sealing may be performed in a temperature range which is 10 to 60° C. lower than a sintering temperature of the solid electrolyte.

When the first heat treatment uses a green sheet in the stacking of the solid electrolyte, a heat treatment for joining and sealing is performed in a temperature range of a sintering temperature of the solid electrolyte to a temperature which is 50° C. lower than the sintering temperature of the solid electrolyte.

The heat treatment may be performed for 3 to 8 hours in the first heat treatment.

According to the solid electrolyte $CO_2$ sensor of various embodiments of the present invention, there is an effect of suppressing a side reaction of moisture due to the improvement in sealing performance and providing a solid electrolyte $CO_2$ sensor which monitors $CO_2$ in real time.

According to the method for manufacturing a solid electrolyte $CO_2$ sensor according to various embodiments of the present invention, there is another effect of providing a method for manufacturing a solid electrolyte $CO_2$ sensor, which simplifies the manufacturing system and reduces the manufacturing costs thereof by omitting the sealing in the manufacturing process.

It is understood that the term "vehicle" or "vehicular" or other similar terms as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g., fuel derived from resources other than petroleum). As referred to herein, a hybrid vehicle is a vehicle that has two or more sources of power, for example, both gasoline-powered and electric-powered vehicles.

The methods and apparatuses of the present invention have other features and advantages which will be apparent from or are set forth in more detail in the accompanying drawings, which are incorporated herein, and the following Detailed Description, which together serve to explain certain principles of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Various embodiments of the present invention are directed to providing a solid electrolyte $CO_2$ sensor and a manufacturing method thereof in order to solve the above-described problems in the related art, and corresponds to a solid electrolyte $CO_2$ sensor when viewed according to various aspects.

Figure 1:
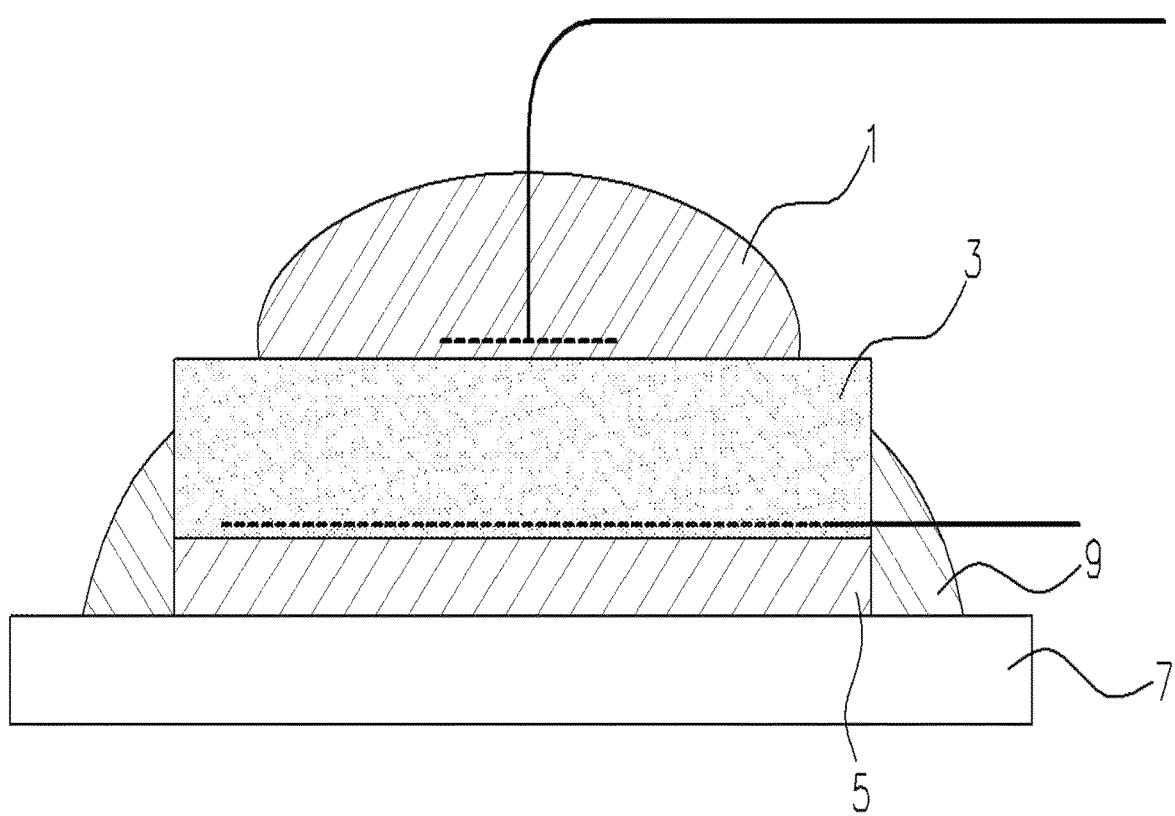
FIG. 1 is a cross-sectional configuration view of a solid electrolyte gas sensor according to the related art.

FIG. 1 is a cross-sectional configuration view of a solid electrolyte gas sensor according to the related art. The gas sensor has a structure in which a substrate 7, a reference electrode 5, a solid electrolyte 3, and a sensing electrode 1 are sequentially stacked, and the side surfaces of the substrate 7, the reference electrode 5, and the solid electrolyte 3 are sealed with a sealing material 9, that is, an Na/Li glass or a ceramic sealant as illustrated in FIG. 1. The solid electrolyte gas sensor as illustrated in FIG. 1 has problems in that a lifting phenomenon, cracks and the like occur because the sealing material part is not compactly joined, attachment and durability deteriorate due to the aforementioned problems, and the reliability for the concentration of gas sensed due to the reaction of infiltrating moisture caused by the occurrence of chasms due to the cracks and the like with the reference electrode deteriorates.

Figure 2:
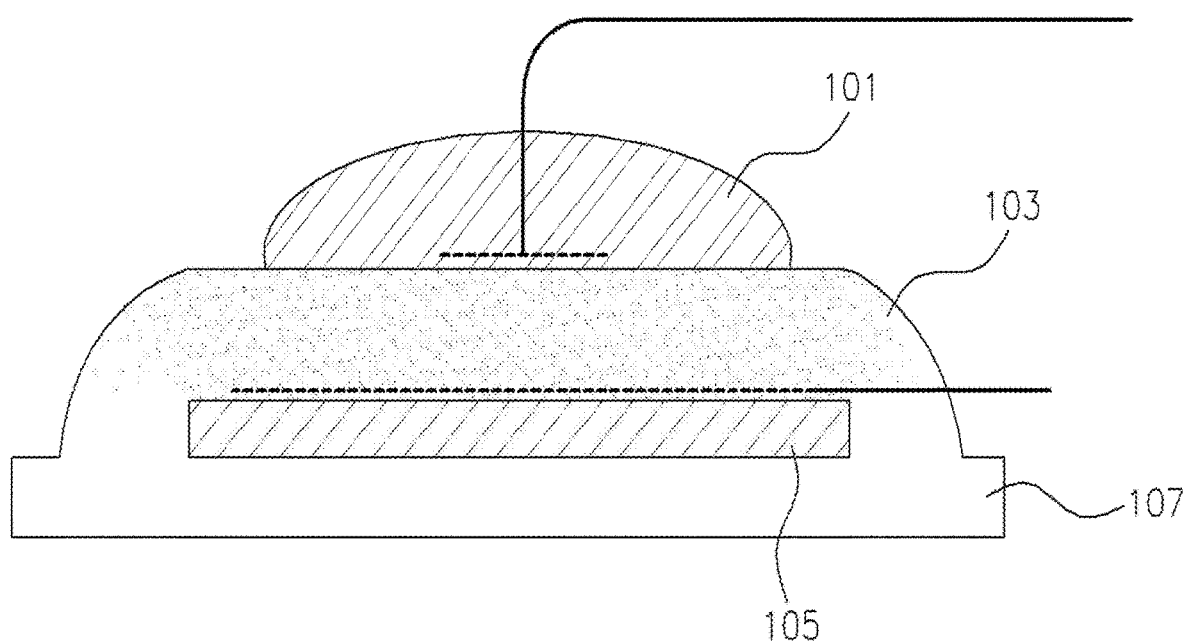
FIG. 2 is a cross-sectional configuration view of a solid electrolyte $CO_2$ sensor according to various embodiments of the present invention.

According to various embodiments of present invention, a solid electrolyte $CO_2$ sensor includes a solid electrolyte 103 which is bonded to a substrate 107 to join and seal the substrate 107, a sensing electrode 101 which is formed at one side of the solid electrolyte 103, and a reference electrode 105 which is formed between the other side of the solid electrolyte 103 and one surface of the substrate 107 and sealed by the solid electrolyte 103 and the substrate 107, and FIG. 2 illustrates a cross-sectional configuration view of a solid electrolyte $CO_2$ sensor according to an various embodiments of the present invention. In various embodiments of the present invention, the reference electrode 105 is stacked on the substrate 107, and the solid electrolyte 103 is stacked on the reference electrode 105. Further, the present invention has a structure in which a sensing electrode 101 is stacked on the solid electrolyte 103, and a structure in which the solid electrolyte 103 and the substrate 107 are reacted with each other by a heat treatment and are joined and sealed with each other. The present invention has an effect of improving the reliability for the measurement of the concentration of $CO_2$ by moisture because attachment and curability may be improved while the reference electrode 105 and the substrate 107 are compactly sealed by the solid electrolyte 103, and chasms are not generated, and thus moisture may be perfectly blocked from infiltrating to prevent the reference electrode 105 and moisture from being reacted, due to the structure as illustrated in FIG. 2.

In various embodiments of the present invention, the reference electrode 105 is a two phase mixture of Li(Na)—Ti(Fe)—O systems or Pt(Au), and the sensing electrode 101 is preferably any one of $A_2CO_3$ (A=Li, Na) or a mixture of $A_2CO_3$ (A=Li, Na) and $BCO_3$ (B=Ba, Ca, Sr). Further, the solid electrolyte 103 is $Na_{1+x}Zr_2Si_xP_{3-x}O_{12}$, and 0<X<3, and the solid electrolyte 103 is $Li_{2+2x}Zn_{1-x}GeO_4$, and 0<X<1. In addition, the substrate 107 is preferably alumina or mullite.

Figure 16:
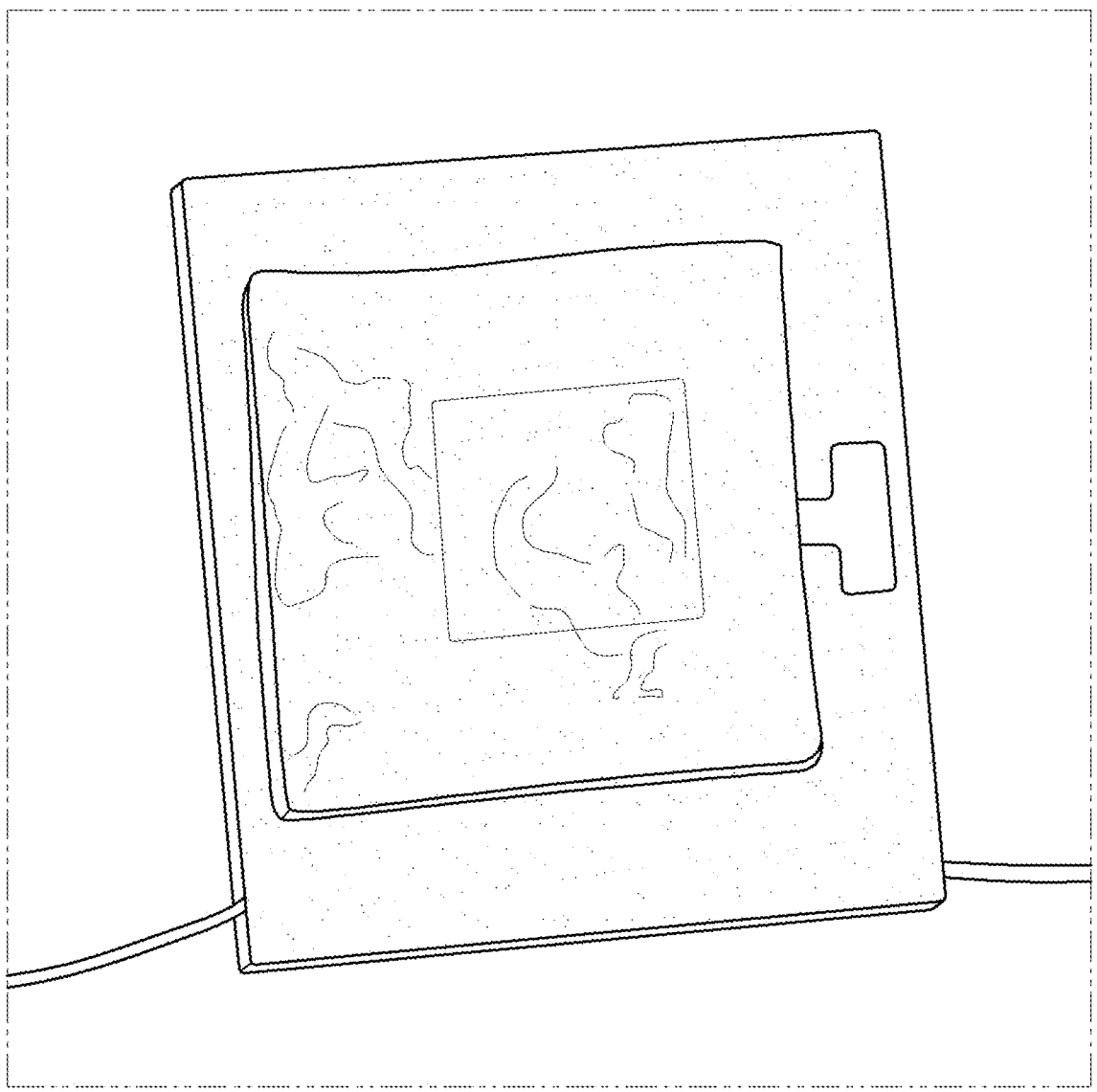
FIG. 16 is an experimental photograph of a solid electrolyte $CO_2$ sensor when the solid electrolyte has a thickness of less than 200 μm.
Figure 17:
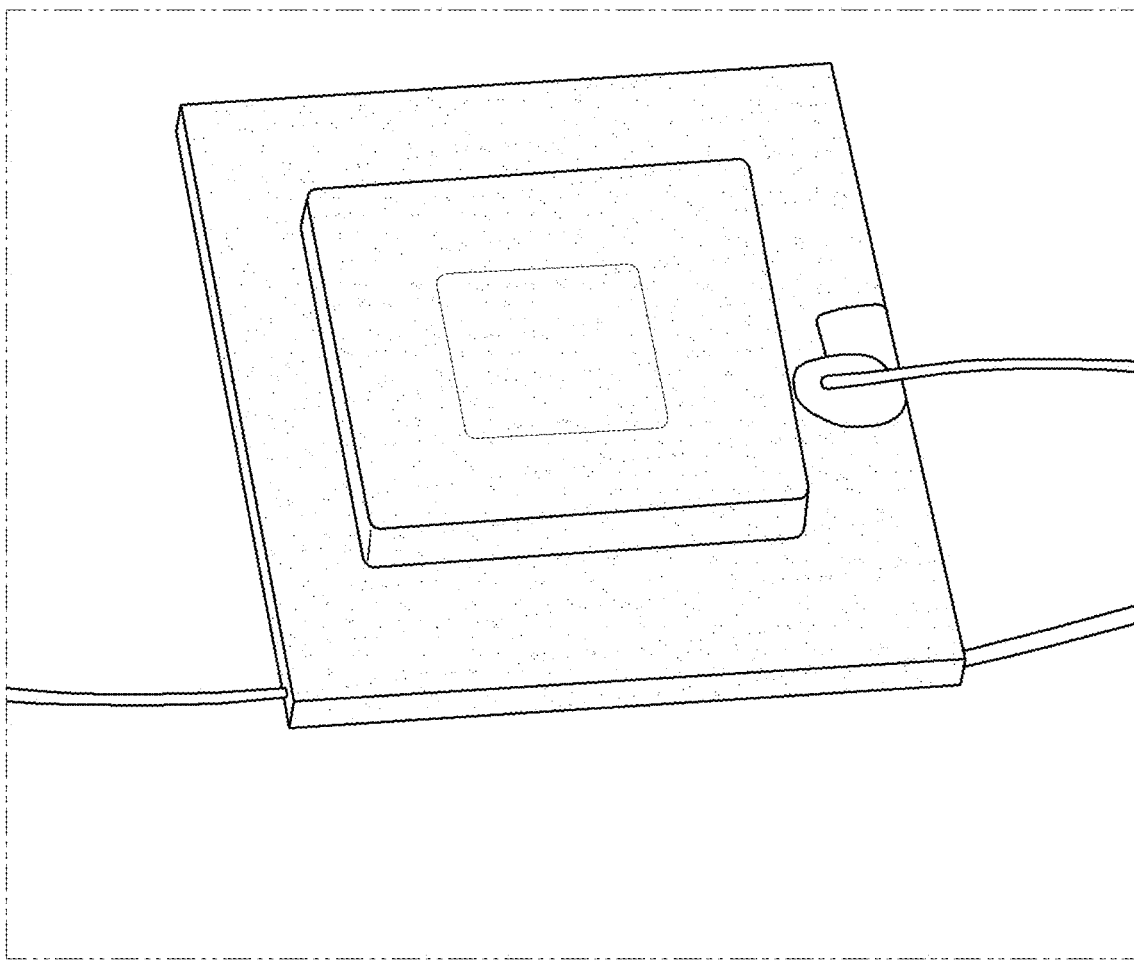
FIG. 17 is an experimental photograph of a solid electrolyte $CO_2$ sensor when the solid electrolyte has a thickness of more than 400 μm.

In various embodiments of the present invention, the solid electrolyte 103 has a thickness of preferably 200 to 400 µm. FIG. 16 is an experimental photograph of a solid electrolyte $CO_2$ sensor when the solid electrolyte 103 has a thickness of less than 200 µm. If the solid electrolyte 103 has a thickness of less than 200 µm, the solid electrolyte 103 is so thin as illustrated in FIG. 16 that there are problems in that the solid electrolyte 103 becomes molten and flows, so that properties of the electrolyte fail to be maintained, and it becomes difficult to operate the sensor because the electrode is covered with the solid electrolyte 103. Further, FIG. 17 is an experimental photograph of a solid electrolyte $CO_2$ sensor when the solid electrolyte 103 has a thickness of more than 400 µm. When the thickness exceeds 400 µm, there are problems in that the solid electrolyte 103 is not joined with the substrate 107 and is lifted as illustrated in FIG. 17, and the reliability of the sensor deteriorates due to the large difference in temperature between an upper surface and a lower surface of the electrolyte.

Figure 18:
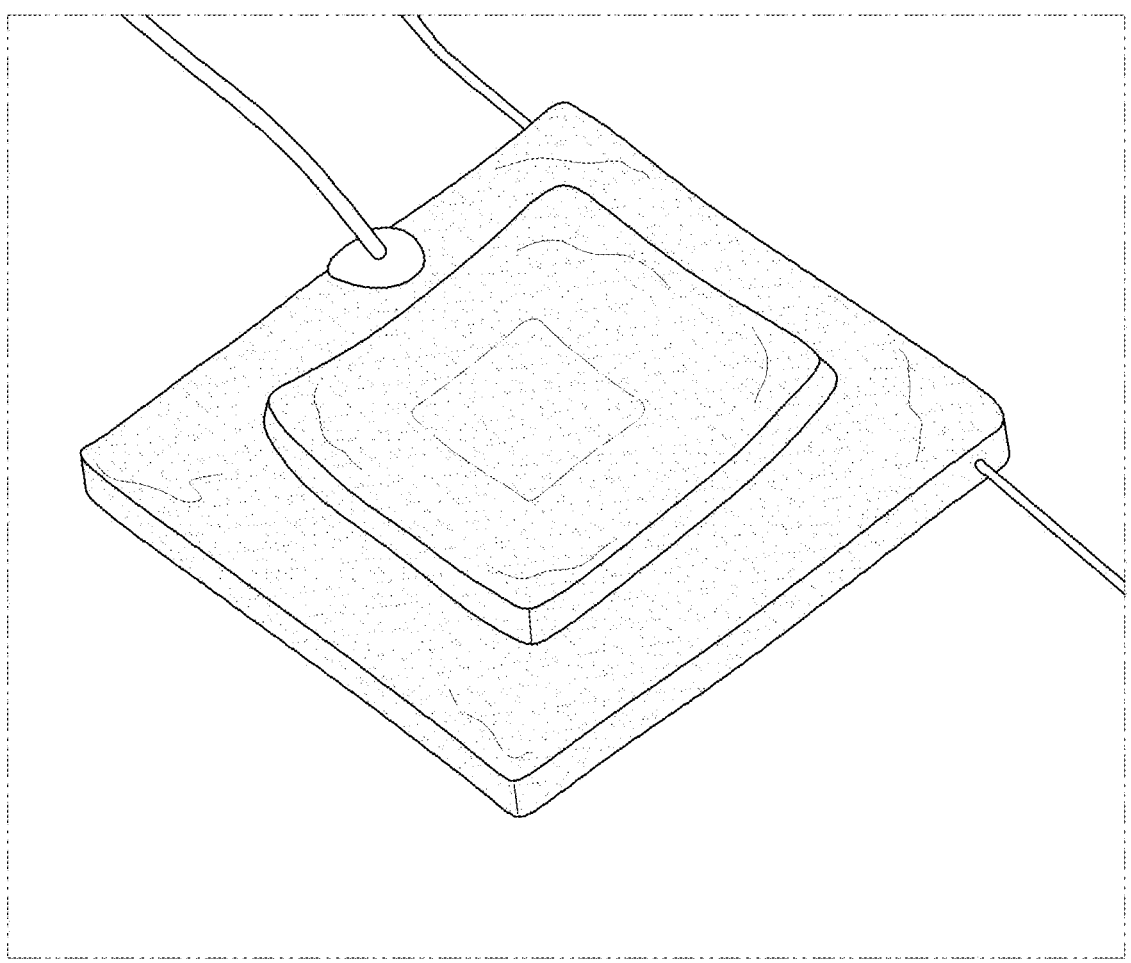
FIG. 18 is a photograph of a solid electrolyte $CO_2$ sensor when an area of a solid electrolyte which is bonded to the substrate and does not join and seal the substrate is less than 20% of an area of the entire solid electrolyte.

Meanwhile, in various embodiments of the present invention, an area of the solid electrolyte 103 which is bonded to the substrate 107 and does not join and seal the substrate 107 is preferably 20 to 90% of an area of the entire solid electrolyte 103. FIG. 18 is a photograph of a solid electrolyte $CO_2$ sensor when an area (area of a non-reaction layer) of the solid electrolyte 103 which is bonded to the substrate 107 and does not join and seal the substrate 107 is less than 20% of an area of the entire solid electrolyte 103. If the area (area of a non-reaction layer) of the solid electrolyte 103 which is bonded to the substrate 107 and does not join and seal the substrate is less than 20% of an area of the entire solid electrolyte 103, a phenomenon in which stress imposed on the solid electrolyte 103 is not relieved and the substrate 107 is bent upward is generated as illustrated in FIG. 18. Further, when the area (area of a non-reaction layer) of the solid electrolyte 103 which is bonded to the substrate 107 and does not join and seal the substrate 107 is more than 90% of an area of the entire solid electrolyte 103, there are problems in that the reaction incompletely occurs because the solid electrolyte 103 and the substrate 107 are not sufficiently brought in contact with each other, and the sealing performance deteriorates.

Meanwhile, in a half cell reaction of the solid electrolyte $CO_2$ sensor which is the present invention, the reaction of the sensing electrode is the same as the following Chemical Formula 1.

$$2Na_{sensing\ electrode} + CO_2 + \tfrac{1}{2}O_2 \rightarrow Na_2CO_3 \quad \text{[Chemical Formula 1]}$$

Furthermore, the reaction of the reference electrode is the same as the following Chemical Formula 2.

$$2Na_{reference\ electrode} + \tfrac{1}{2}O_2 \rightarrow Na_2O_{solid\ electrolyte} \quad \text{[Chemical Formula 2]}$$

The entire electrode reaction, which synthesizes the reaction, is the same as the following Chemical Formula 3.

$$Na_2O + CO_2 \rightarrow Na_2CO_3 \quad \text{[Chemical Formula 3]}$$

The reaction formula for the electromotive force in this regard is the same as the following Equation 1.

Electromotive Force [Equation 1]

$$V = -\frac{1}{2F}\Delta G^{rxn} + \frac{RT}{2F}\ln\frac{a_{CO_2}}{\frac{a_{Na_2CO_3}}{a_{Na_2O}}}$$

In Equation 1 for the electromotive force, $\Delta G^{rxn}$ corresponds to the reaction energy of the entire electrode reaction. Further, $a_{CO_2}$ is the activity of carbon dioxide ($CO_2$), and $a_{Na_2CO_3}$ corresponds to the activity of $Na_2CO_3$ and $a_{Na_2O}$ corresponds to the activity of $Na_2O$. Further, the activity is proportional to the concentration. In this case, in order to measure the concentration of carbon dioxide by the electromotive force of the solid electrolyte $CO_2$ sensor, the electromotive force needs to be the same as the functional relationship of the electromotive force according to the activity of carbon dioxide, that is, the following Equation 2.

Electromotive force $V = f(a_{CO_2})$ [Equation 2]

Ultimately, in order to obtain the same result as Equation 2, $a_{Na_2CO_3}$ and $a_{Na_2O}$ need to be constant, and $a_{Na_2CO_3}$ is determined by the ratio of the electrode materials, and thus has a predetermined value, and $a_{Na_2O}$ has a predetermined value by the content of Na which NASICON includes.

In the reference electrode of the solid electrolyte $CO_2$ sensor, a side reaction, such as the following Chemical Formula 4, is generated by moisture.

$$Na_2O_{solid\ electrolyte} + H_2O \rightarrow 2NaOH \quad \text{[Chemical Formula 4]}$$

Ultimately, $a_{Na_2O}$ does not have a predetermined value due to the reaction as in Chemical Formula 4 described above, and thus the functional relationship as in Equation 2 is not maintained, and accordingly, there is a problem in that the solid electrolyte $CO_2$ sensor needs to be sealed to improve the reliability.

Figure 23:
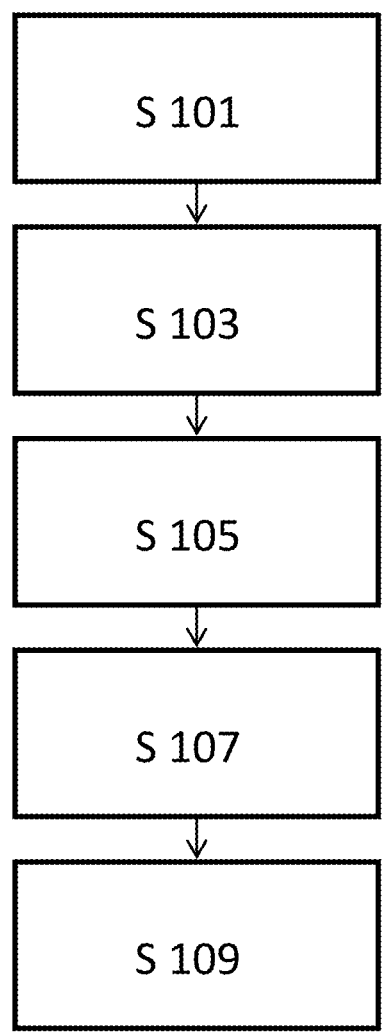
FIG. 23 is a flowchart of a method for manufacturing a solid electrolyte $CO_2$ sensor according to an exemplary embodiment of the present invention.

Meanwhile, various embodiments of the present invention are directed to a method for manufacturing a solid electrolyte $CO_2$ sensor. FIG. 23 is a flowchart of a method for manufacturing a solid electrolyte $CO_2$ sensor according to various embodiments of the present invention. The present invention provides a method for manufacturing a solid electrolyte $CO_2$ sensor, the method including a step of stacking a reference electrode 105 on a substrate 107 (S101), a step of stacking a solid electrolyte 103 having a larger area than the reference electrode 105 stacked on the substrate 107 to stack an end portion of the solid electrolyte on the substrate 107 (S103), a first heat treatment step of subjecting the substrate 107, reference electrode 105, and solid electrolyte 103 which are stacked to heat treatment to join and seal the substrate 107, the reference electrode 105, and the solid electrolyte 103 (S105), a step of stacking a sensing electrode 101 on the stacked solid electrolyte 103 (S107), and a second heat treatment step of performing a heat treatment in order to bond the sensing electrolyte onto the solid electrolyte (S109) as illustrated in FIG. 23.

Figure 3:
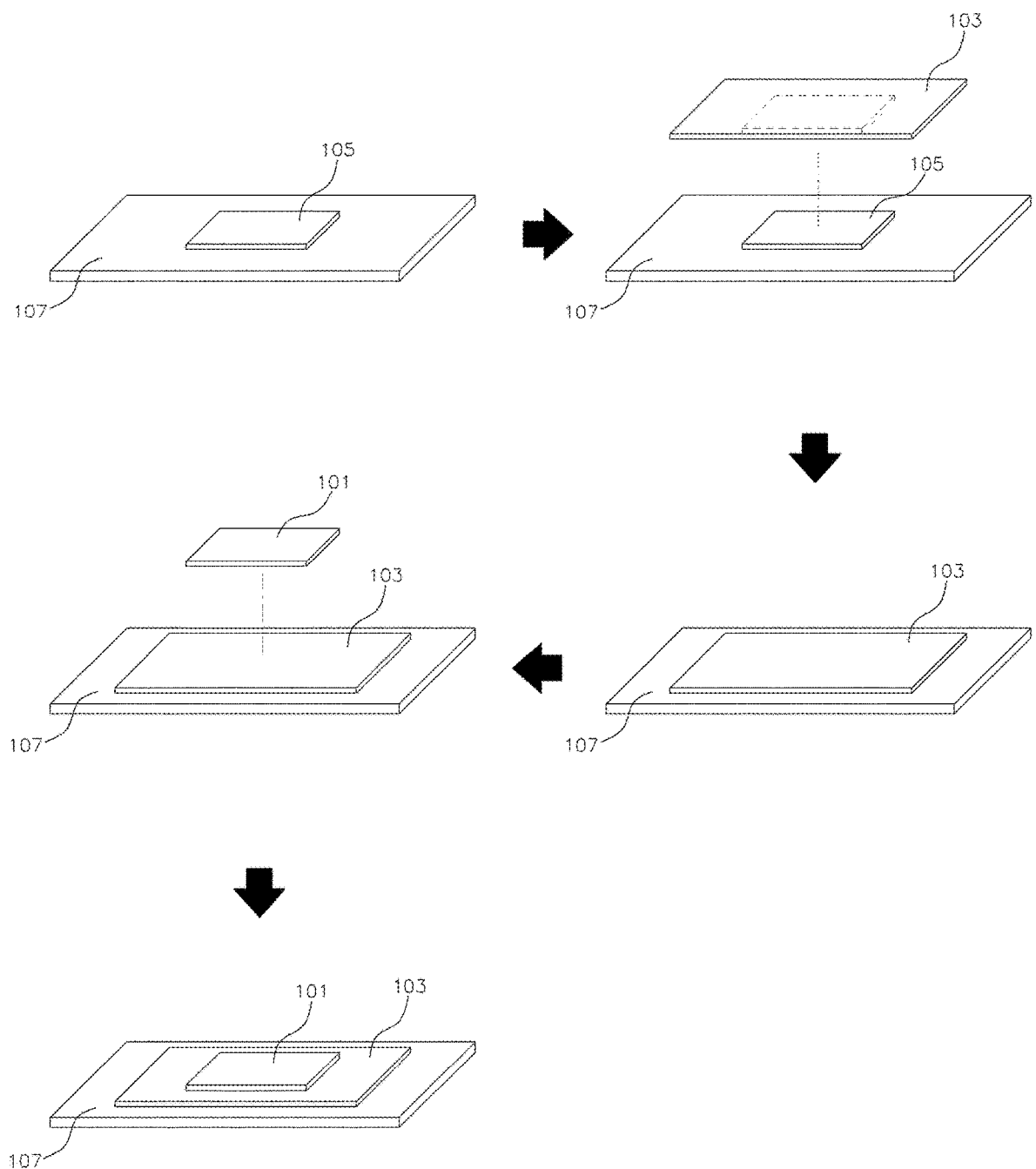
FIG. 3 is a step-by-step configuration view of a method for manufacturing a solid electrolyte $CO_2$ sensor according to various embodiments of the present invention.
Figure 4:
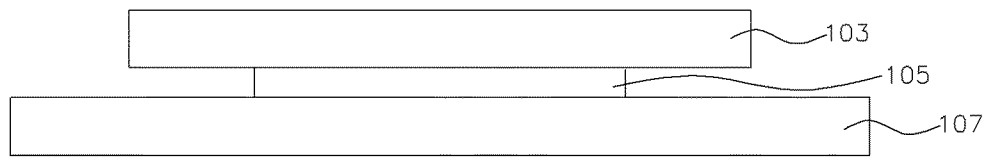
FIG. 4 is a cross-sectional configuration view of a state in which the substrate, the reference electrode and the solid electrolyte according to various embodiments of the present invention are stacked.

When more specifically reviewed, FIG. 3 is a step-by-step configuration view of a method for manufacturing a solid electrolyte $CO_2$ sensor according to various embodiments of the present invention. The reference electrode 105 is stacked on the substrate 107, and then the solid electrolyte 103 is stacked on the reference electrode 105. In this case, the stacking is conducted such that the solid electrolyte 103 may completely cover the reference electrode 105 and the end portion of the solid electrolyte may be overlapped with the substrate 107. FIG. 4 is a cross-sectional configuration view of a state in which the substrate 107, the reference electrode 105 and the solid electrolyte 103 according to various embodiments of the present invention are stacked. In FIG. 4, it can be confirmed that the solid electrolyte 103 and the substrate 107 completely cover the reference electrode 105 and the substrate 107 and the end portion of the solid electrolyte are overlapped with each other. And then, the substrate 107, reference electrode 105 and solid electrolyte 103 stacked as illustrated in FIG. 4 are joined and sealed by a heat treatment. And then, a sensing electrode 101 is stacked on the solid electrolyte 103, and then the heat treatment is performed to join the sensing electrode 101 with the solid electrolyte 103.

In the method for manufacturing a solid electrolyte $CO_2$ sensor according to various embodiments of the present invention, the reference electrode 105 is preferably a two phase mixture of Li(Na)—Ti(Fe)—O systems or Pt(Au), and is preferably any one of $A_2CO_3$ (A=Li, Na) or a mixture of $A_2CO_3$ (A=Li, Na) and $BCO_3$ (B=Ba, Ca, Sr). Further, the solid electrolyte 103 has a thickness of preferably 200 to 400 μm, and the solid electrolyte 103 is preferably $Na_{1+x}Zr_2Si_xP_{3-x}O_{12}$, and 0<X<3. Further, the solid electrolyte 103 is preferably $Li_{2+2x}Zn_{1-x}GeO_4$, and 0<X<1, and in the stacking of the solid electrolyte (S103), an area of a solid electrolyte which is bonded to the substrate 107 and does not join and seal the substrate 107 is preferably 20 to 90% of an area of the entire solid electrolyte. In addition, the substrate 107 is preferably alumina or mullite.

Meanwhile, in various embodiments of the present invention, in the stacking of the solid electrolyte (S103), a sintered body or a green sheet is preferably used. In the related art, a substrate 7 is sintered, then a solid electrolyte 3 is sintered, and then the substrate 7 is joined with the solid electrolyte 3 and heat-treated with a sealing material 9 to seal the substrate 7 and the solid electrolyte 3. And then, the step is a step of joining the sensing electrode 1 by heat treatment. However, when a sintered body is used in the present invention, the substrate 107 is sintered, then the solid electrolyte 103 is sintered, and then the sintered substrate 107 and the sintered solid electrolyte 103 are joined and sealed with each other by heat treatment. And then, the sensing electrode 101 is joined by heat treatment to simplify the process compared to the related art. Further, when a green sheet is used in the present invention, it is possible to obtain an effect of further simplifying the process compared to the related art by sintering the substrate 107, then joining and sealing the sintered substrate 107 and the green sheet, which is a solid electrolyte by heat treatment, and then joining the sensing electrode 101 by heat treatment.

In the first heat treatment step (S105) in the present invention, when a sintered body is used in the stacking of the solid electrolyte (S103), it is preferred to perform joining and sealing by a heat treatment in a temperature range which is 10 to 60° C. lower than the sintering temperature of the solid electrolyte, and in the first heat treatment step (S105), when a green sheet is used in the stacking of the solid electrolyte (S103), it is preferred to perform joining and sealing by a heat treatment in a temperature range of a sintering temperature of the solid electrolyte to a temperature which is 50° C. lower than the sintering temperature of the solid electrolyte, and in the first heat treatment step (S105), it is preferred to perform a heat treatment for 3 to 8 hours.

EXAMPLES

Hereinafter, various embodiments of the present invention will be described in more detail through the Examples. These Examples are only for exemplifying various embodiments of the present invention, and it will be obvious to the person with ordinary skill in the art that the scope of various embodiments of the present invention is not interpreted to be limited by these Examples.

Figure 5:
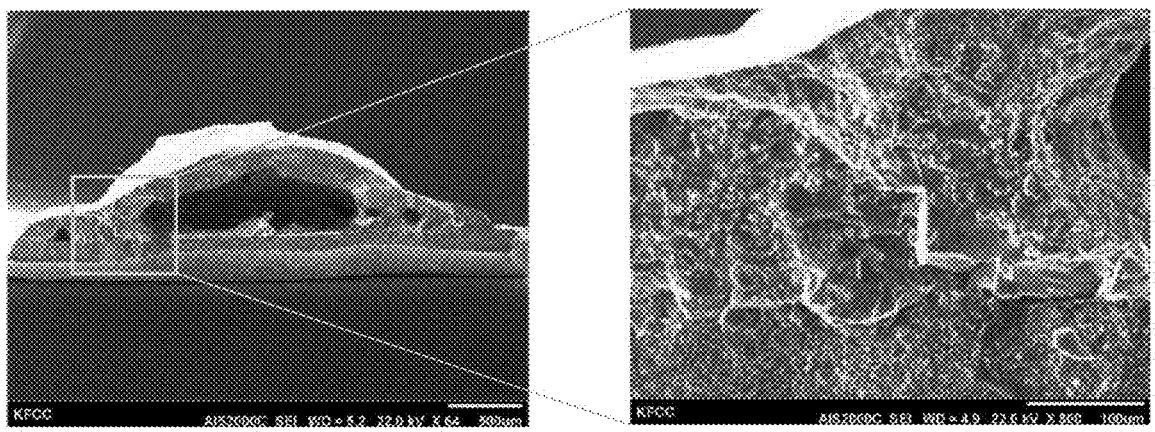
FIG. 5 is a photograph of a solid electrolyte $CO_2$ sensor using a sintered body which is a solid electrolyte according to various embodiments of the present invention and an enlarged photograph of a joining and sealing part.
Figure 6:
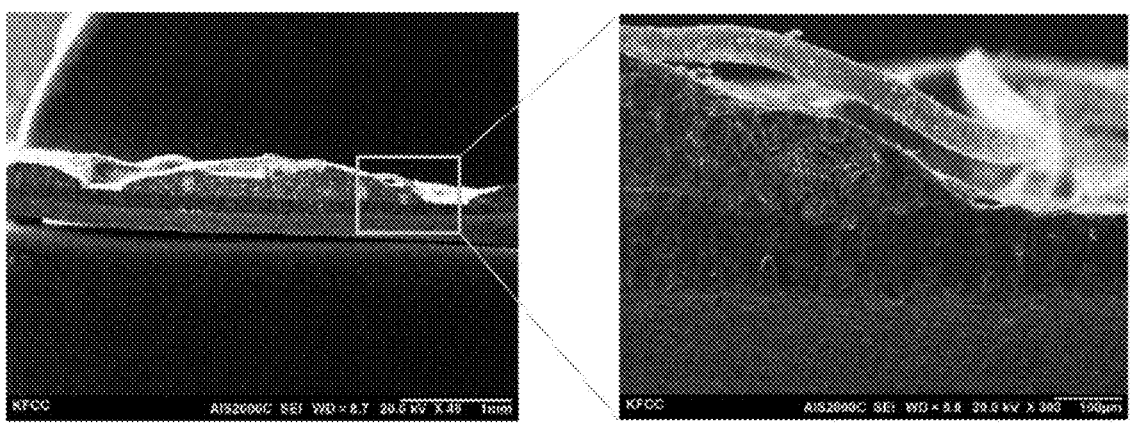
FIG. 6 is a photograph of a solid electrolyte $CO_2$ sensor using a green sheet which is a solid electrolyte according to various embodiments of the present invention and an enlarged photograph of a joining and sealing part.

FIG. 5 is a photograph of a solid electrolyte $CO_2$ sensor using a sintered body which is a solid electrolyte 103 according to various embodiments of the present invention and an enlarged photograph of a joining and sealing part, and FIG. 6 is a photograph of a solid electrolyte $CO_2$ sensor using a green sheet which is a solid electrolyte 103 according to various embodiments of the present invention and an enlarged photograph of a joining and sealing part.

As illustrated in FIGS. 5 and 6, it can be confirmed that in a scanning electron microscope photograph in which NASICON that is a solid electrolyte 103 is joined and sealed with alumina that is a substrate by heat treatment, the alumina and the NASICON are joined and sealed with each other by a reaction, and are compactly adhered to the boundary surface.

Figure 7:
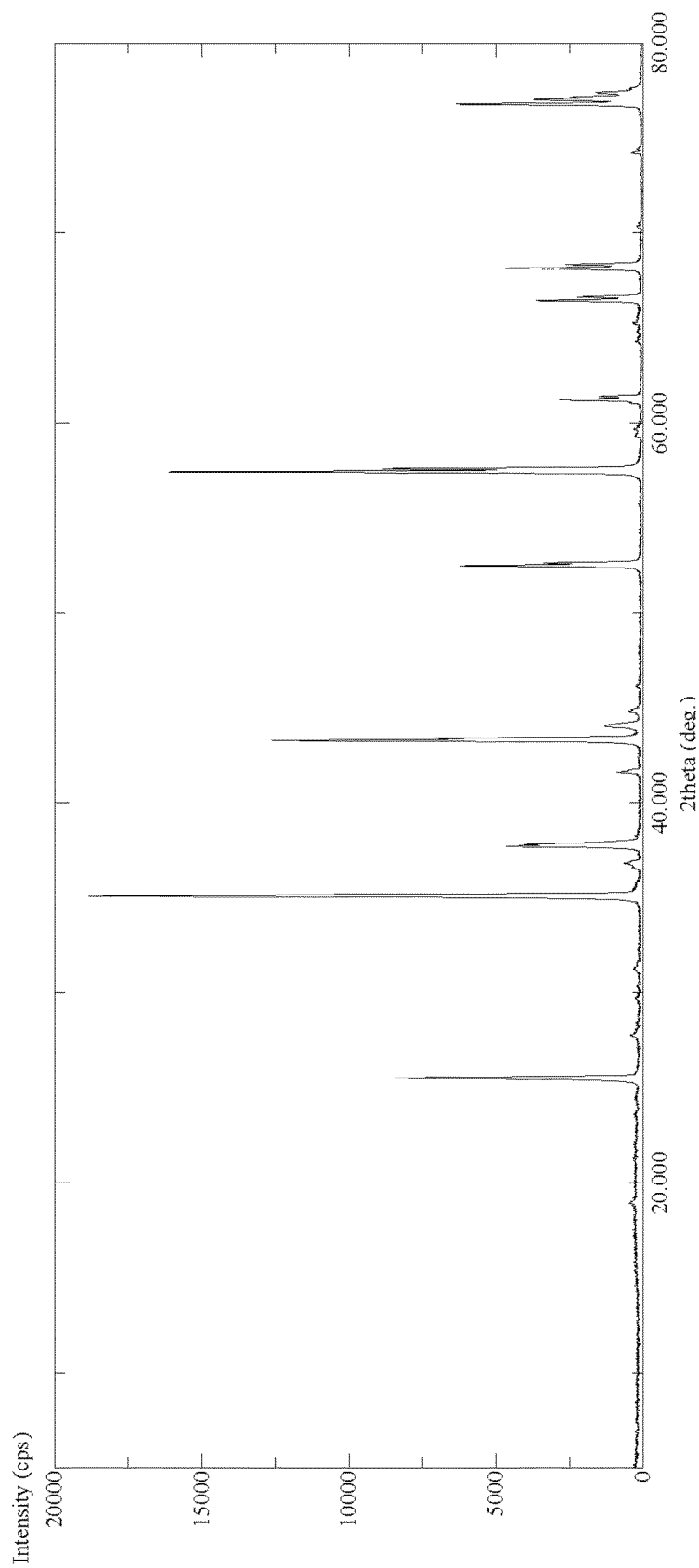
FIG. 7 is an X-ray diffraction graph of an alumina substrate after the alumina substrate is joined and sealed with NASICON ($Na_{1+x}Zr_2Si_xP_{3-x}O_{12}$, X=2) which is a solid electrolyte.
Figure 8:
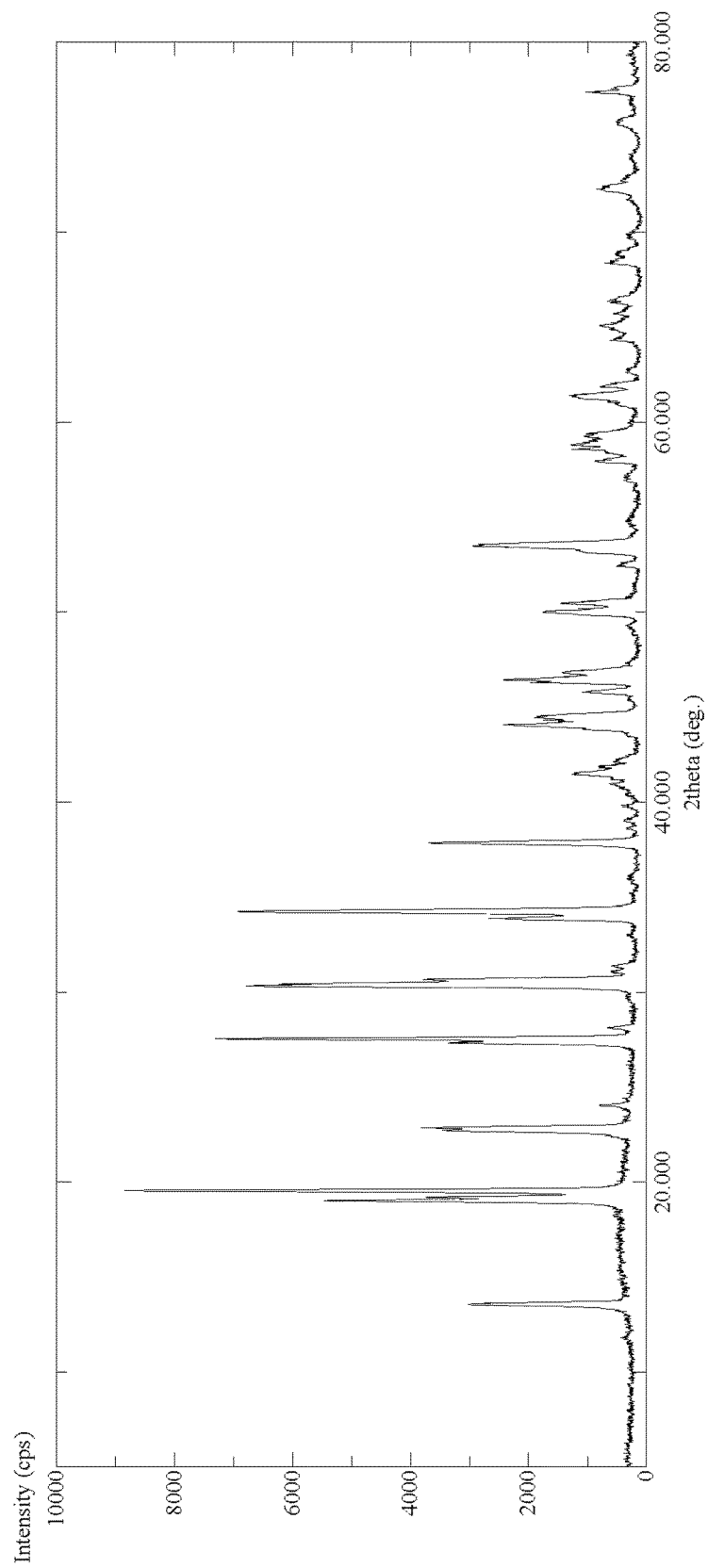
FIG. 8 is an X-ray diffraction graph of NASICON after the alumina substrate is joined and sealed with NASICON which is a solid electrolyte.
Figure 9:
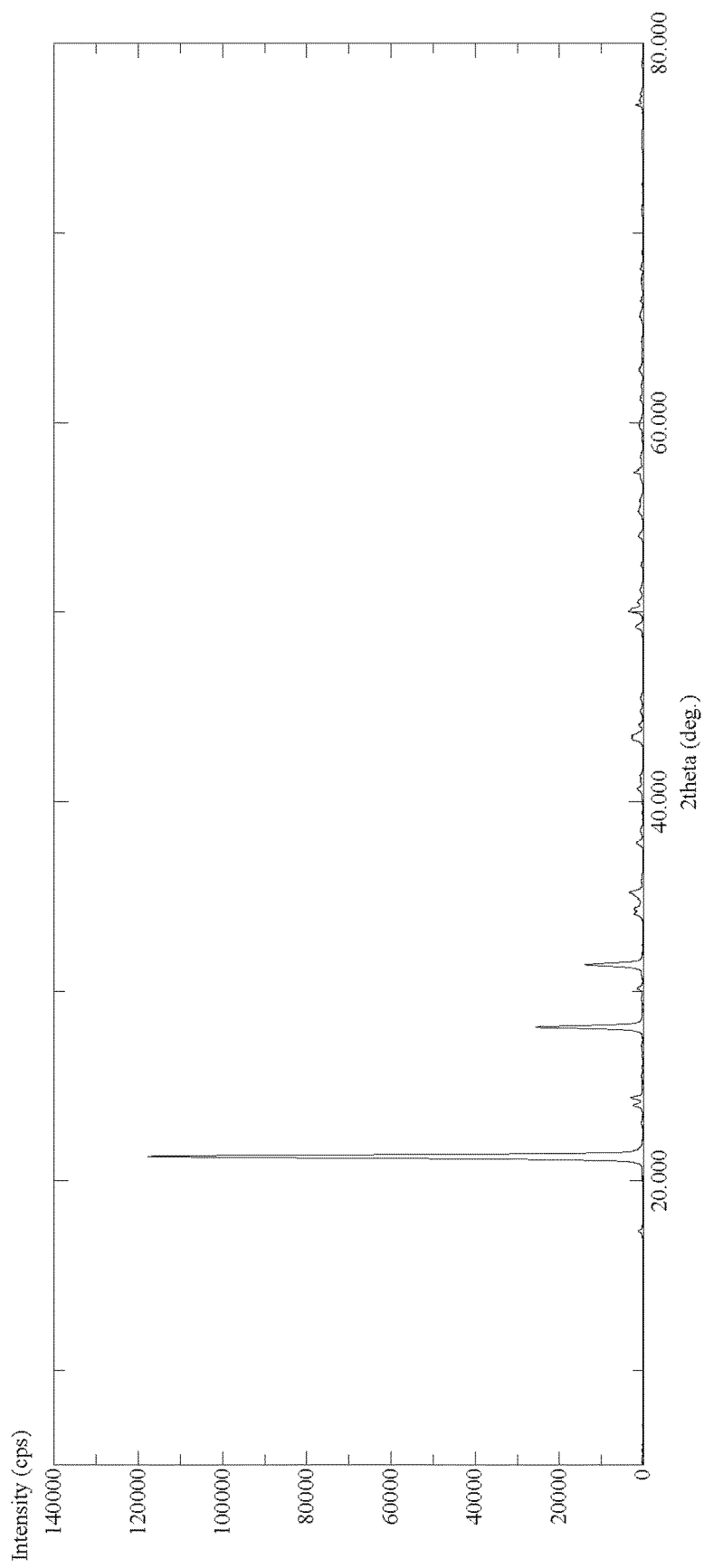
FIG. 9 is an X-ray diffraction graph of a joining and sealing part after the alumina substrate is joined and sealed with NASICON which is a solid electrolyte.

The joining and sealing part, in which the alumina and the NASICON are joined with each other by the reaction, is joined and sealed with a new material other than NASICON or alumina due to the heat treatment. FIG. 7 is an X-ray diffraction graph of an alumina substrate after the alumina substrate is joined and sealed with NASICON which is a solid electrolyte, FIG. 8 is an X-ray diffraction graph of NASICON after the alumina substrate is joined and sealed with NASICON which is a solid electrolyte, and FIG. 9 is an X-ray diffraction graph of a joining and sealing part after the alumina substrate is joined and sealed with NASICON which is a solid electrolyte. From the observation that the heat treatment for joining the alumina with the NASICON is performed, and then the substrate alumina, the solid electrolyte NASICON, and the joining and sealing part of the substrate alumina and the solid electrolyte NASICON have X-ray diffraction values different from each other, it can be confirmed that the materials are different from each other and that due to the heat treatment, a new material other than alumina and NASICON is produced by the reaction.

Figure 10:
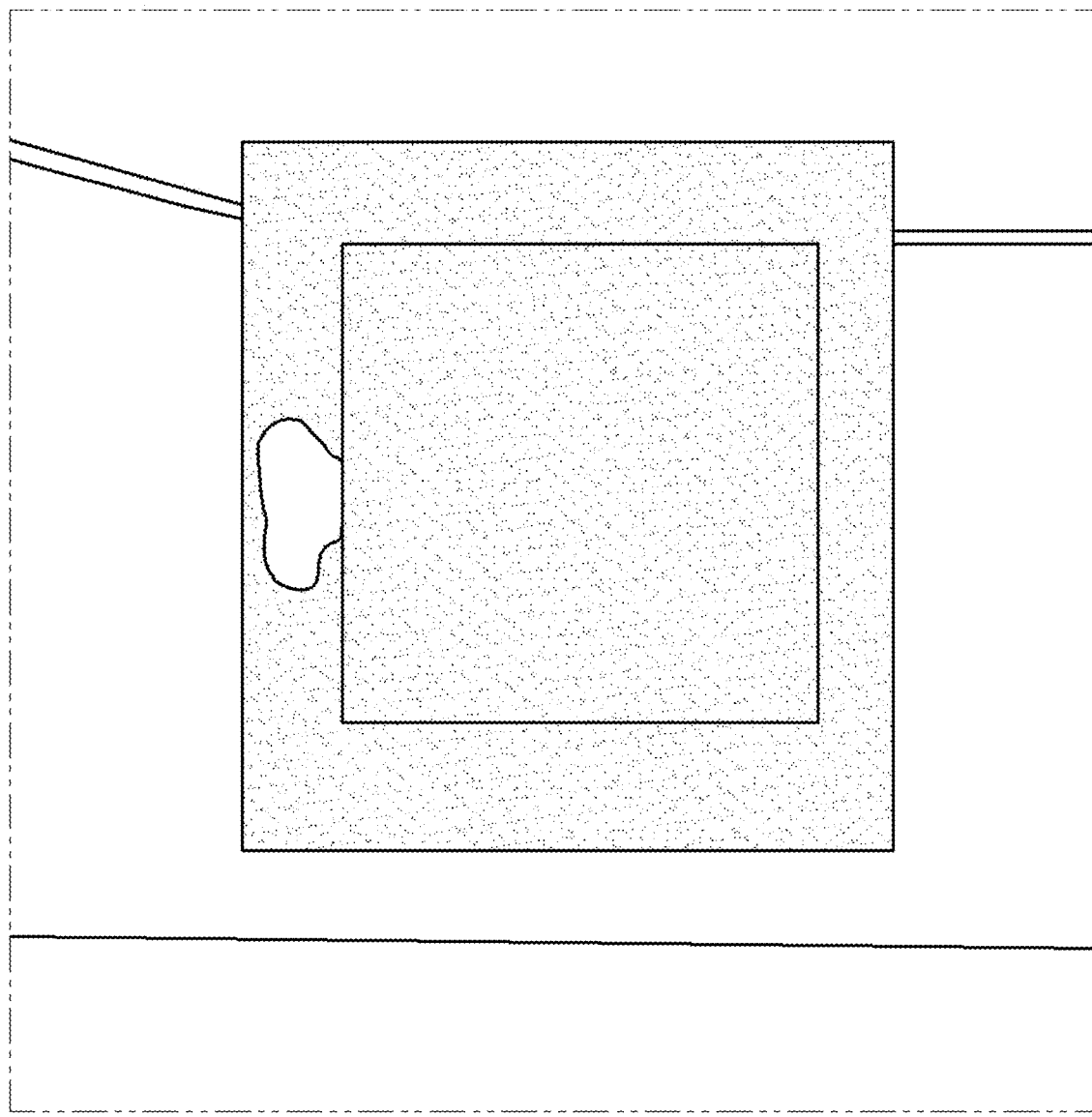
FIG. 10 is an experimental photograph in which the first heat treatment step is performed at a temperature of 1,100° C. in the manufacturing method according to various embodiments of the present invention.
Figure 11:
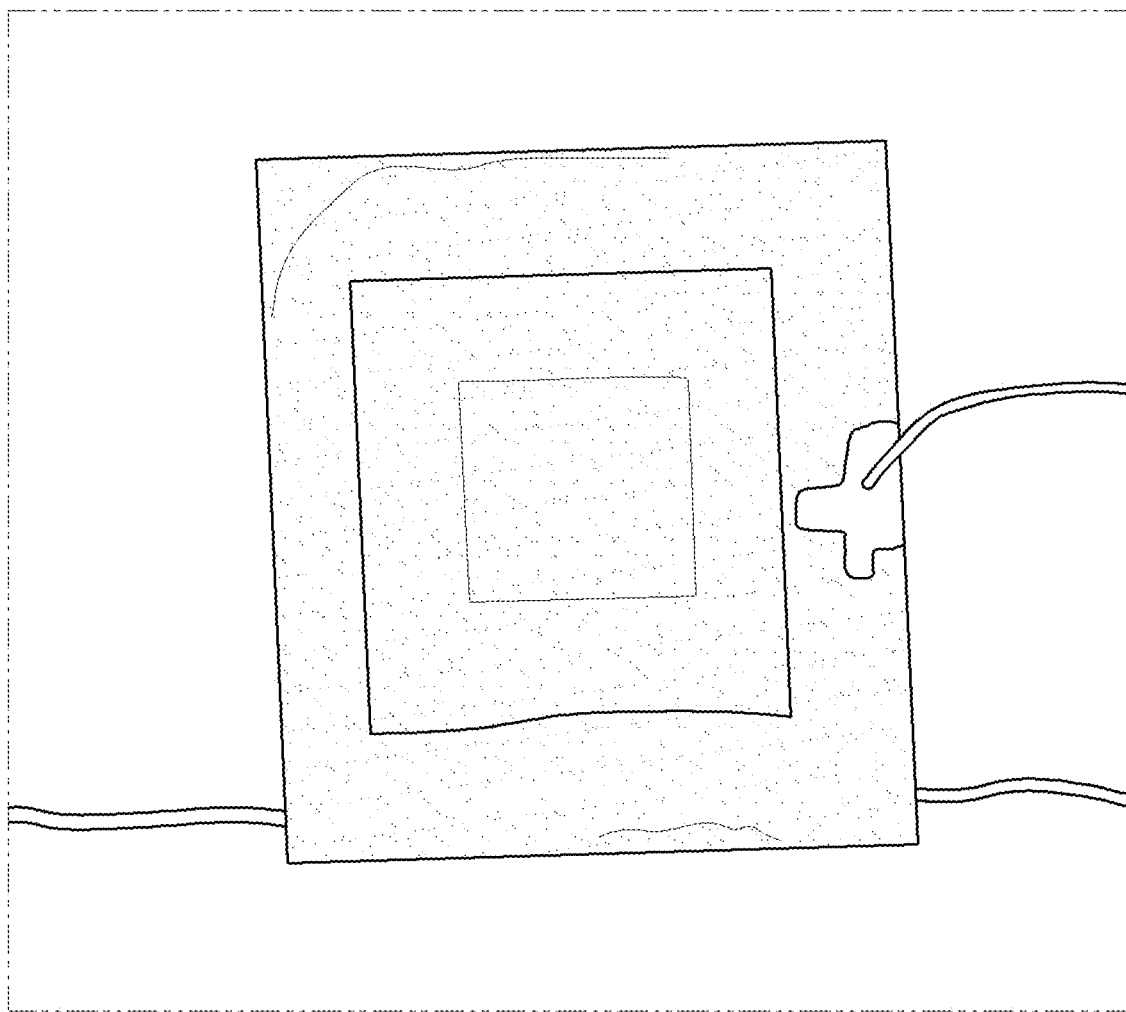
FIG. 11 is an experimental photograph in which the first heat treatment step is performed at a temperature of 1,180° C. in the manufacturing method according to various embodiments of the present invention.
Figure 12:
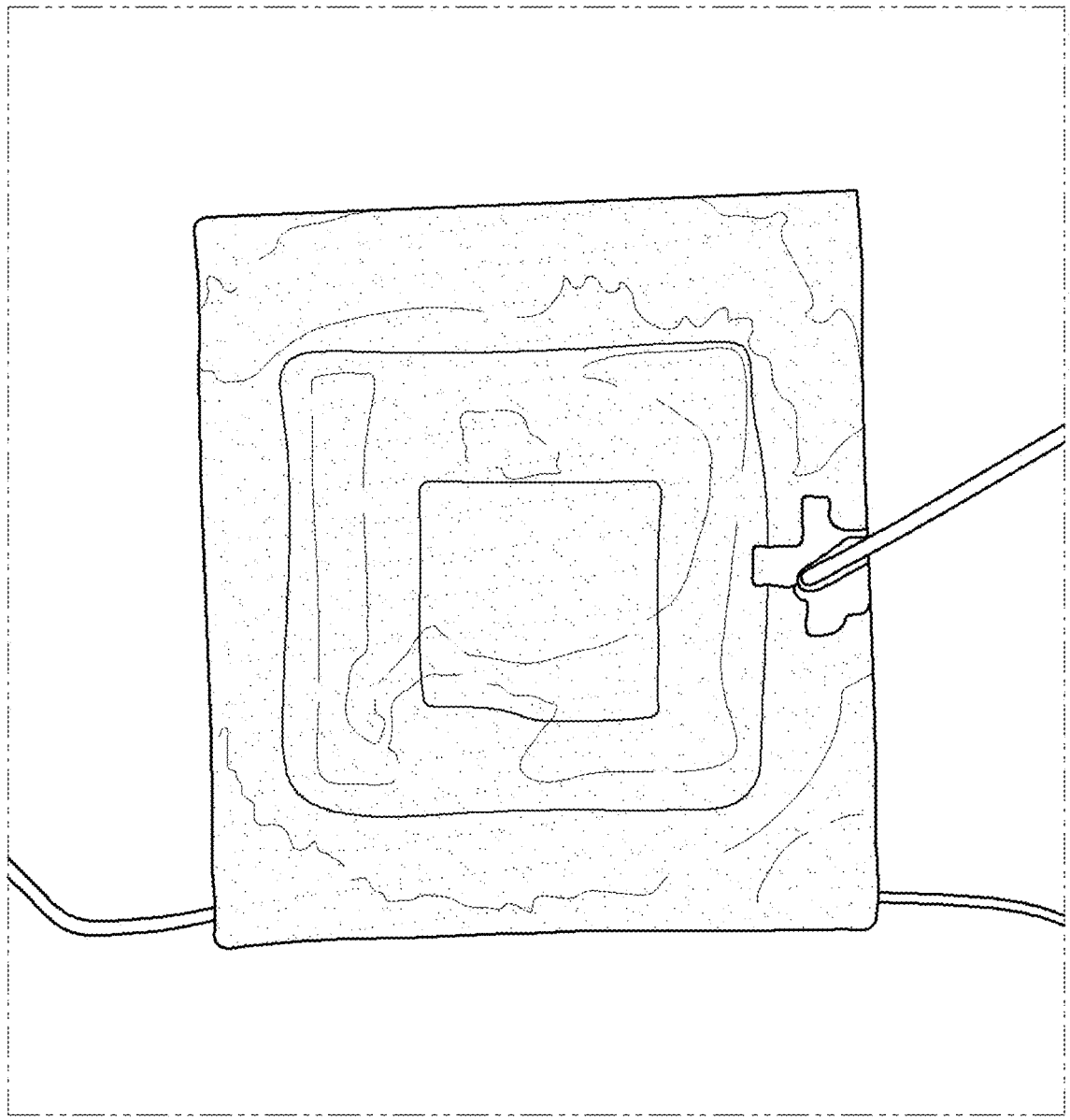
FIG. 12 is an experimental photograph in which the first heat treatment step is performed at a temperature of 1,250° C. in the manufacturing method according to various embodiments of the present invention.

Meanwhile, when the first heat treatment step (S105) uses a sintered body in the stacking of the solid electrolyte (S103), a heat treatment is performed for joining and sealing in a temperature range which is 10 to 60° C. lower than a sintering temperature of the solid electrolyte. FIG. 11 is an experimental photograph in which the first heat treatment step (S105) is performed at a temperature of 1,180° C. in the manufacturing method according to various embodiments of the present invention, and as illustrated in FIG. 11, it can be confirmed that the substrate 107 and the solid electrolyte 103 are joined and sealed with each other. If a heat treatment is performed at a temperature lower than a temperature which is 60° C. lower than the sintering temperature of the solid electrolyte, there occurs a problem in that the solid electrolyte 103 and the substrate 107 are not reacted with each other. FIG. 10 is an experimental photograph in which the first heat treatment step (S105) is performed at a temperature of 1,100° C. in the manufacturing method according to various embodiments of the present invention, and it can be confirmed that the substrate 107 and the solid electrolyte 103 are neither joined nor sealed with each other due to the heat treatment performed at a temperature lower than a temperature which is 60° C. lower than the sintering temperature of the solid electrolyte. Further, when the heat treatment is performed at a temperature higher than a temperature which is 10° C. lower than the sintering temperature of the solid electrolyte 103, there is a problem in that the substrate 107 and the solid electrolyte 103 are overreacted. FIG. 12 is an experimental photograph in which the first heat treatment step (S105) is performed at a temperature of 1,250° C. in the manufacturing method according to various embodiments of the present invention, and as illustrated in FIG. 12, it can be confirmed that the substrate 107 and the solid electrolyte 103 are overreacted.

Figure 13:
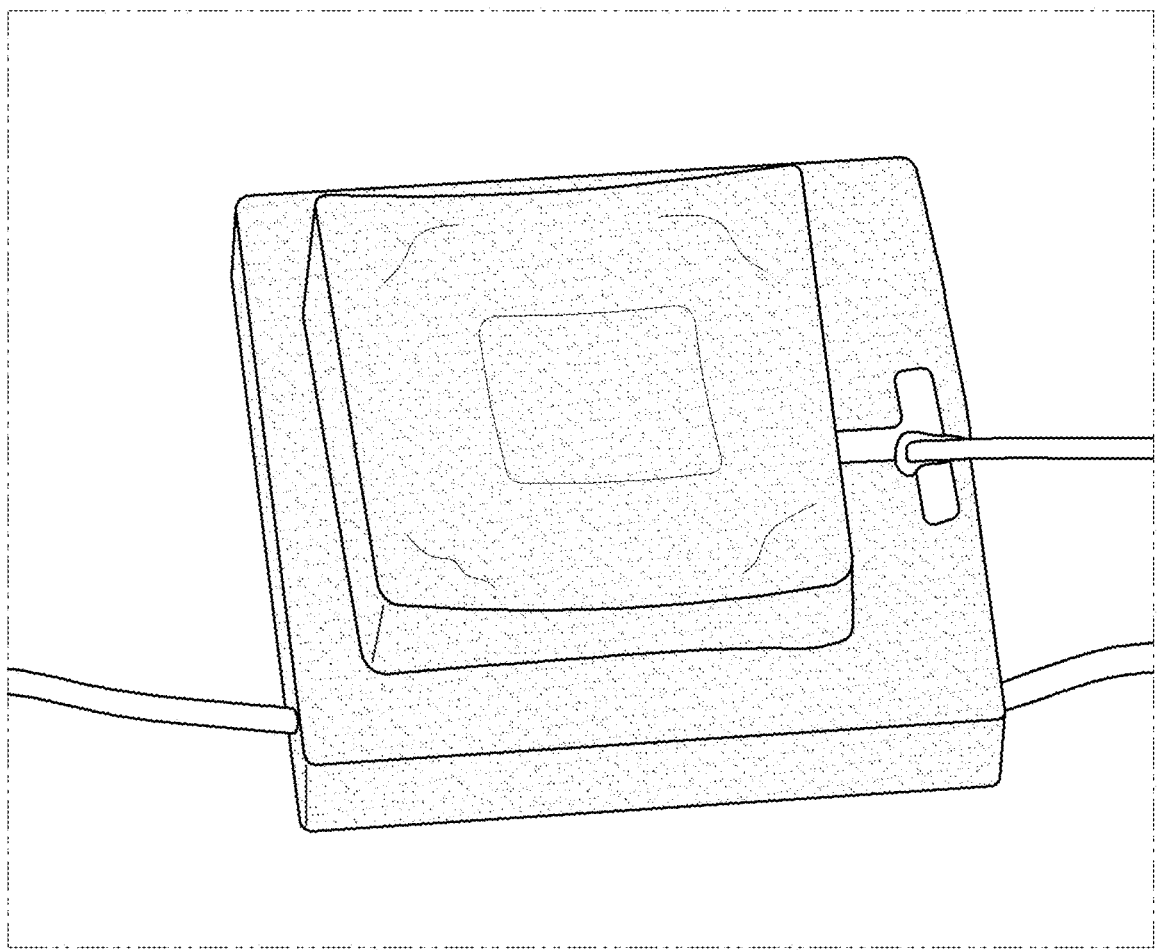
FIG. 13 is an experimental photograph in which the first heat treatment step is performed for 2 hours in the manufacturing method according to various embodiments of the present invention.
Figure 14:
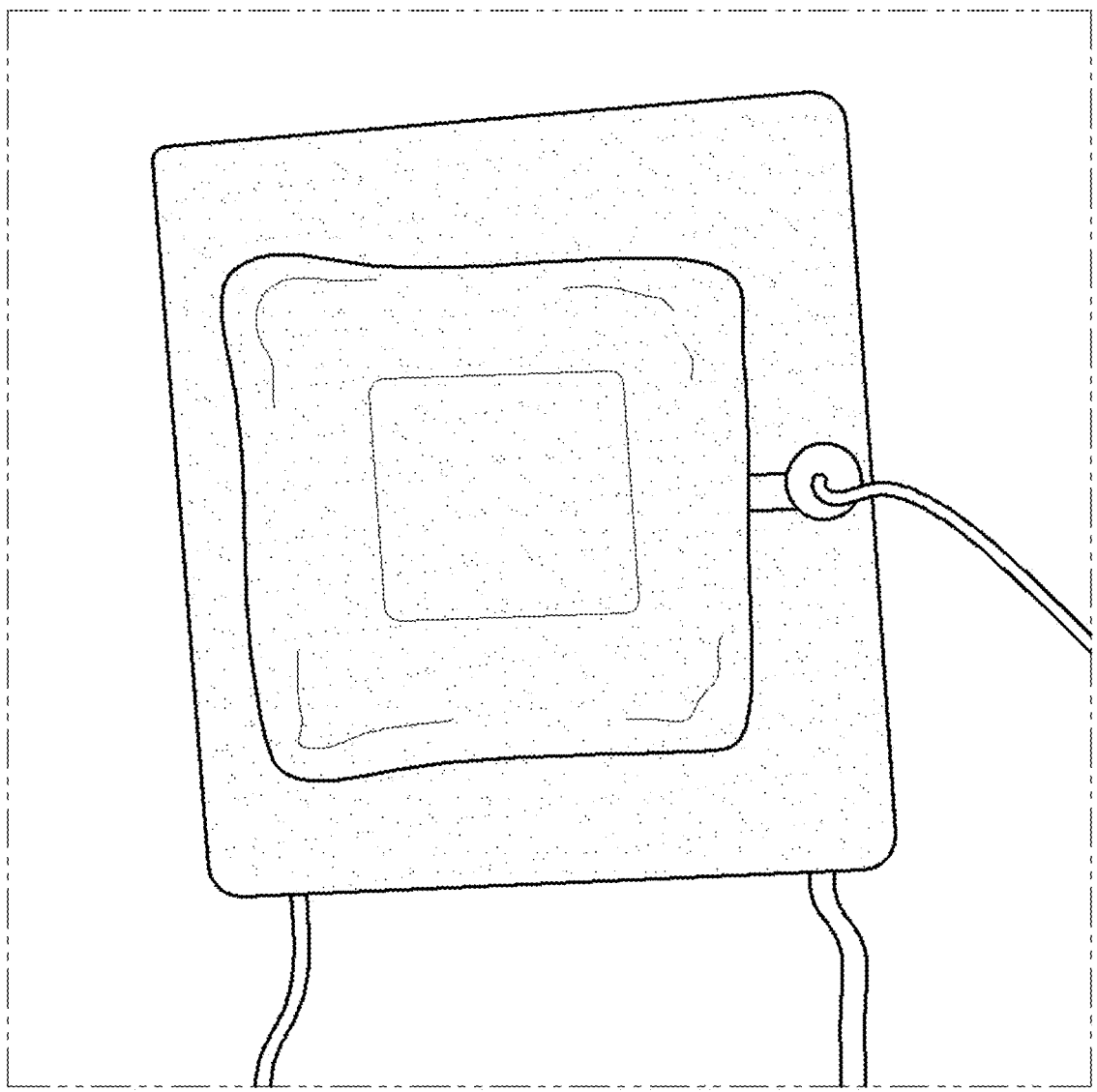
FIG. 14 is an experimental photograph in which the first heat treatment step is performed for 4 hours in the manufacturing method according to various embodiments of the present invention.
Figure 15:
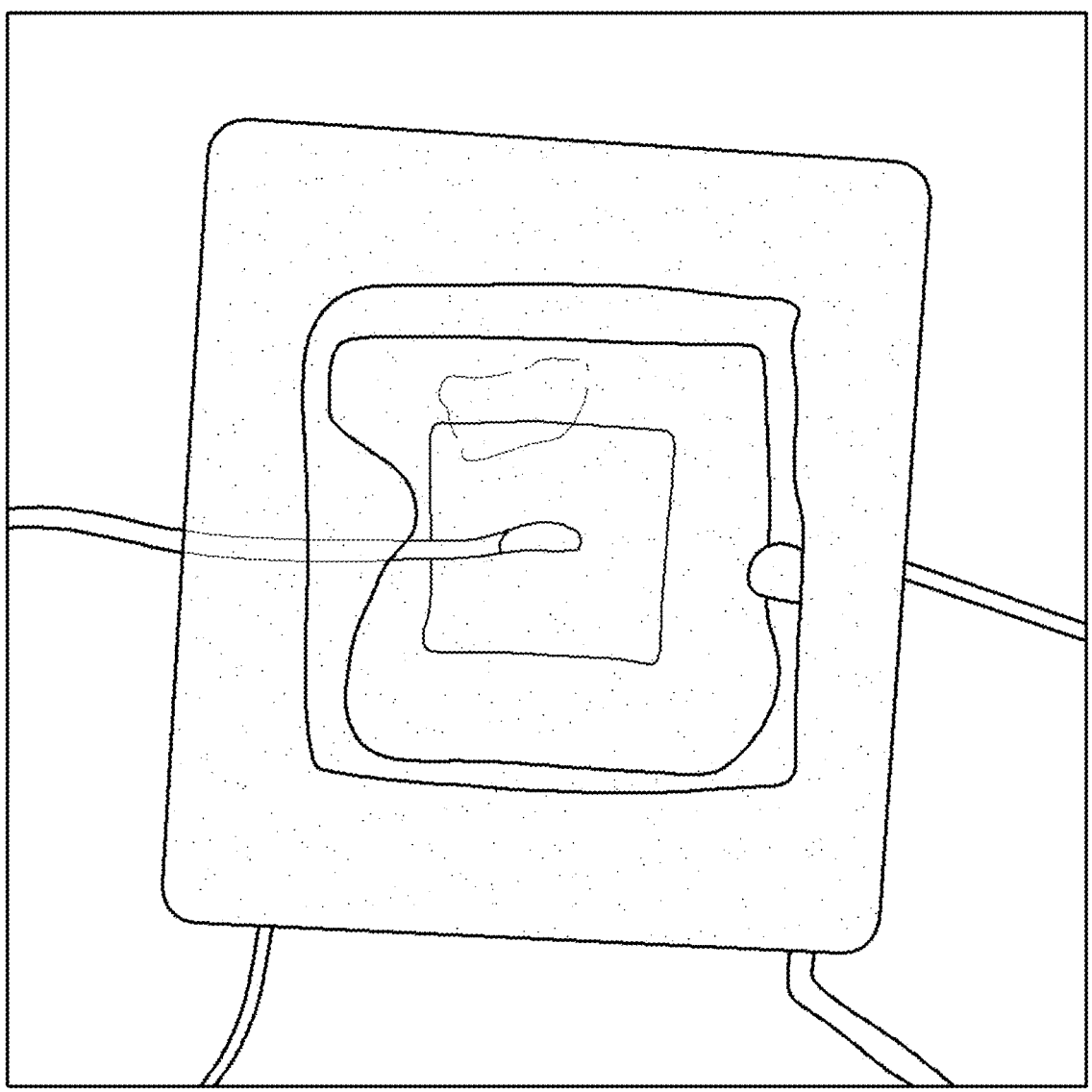
FIG. 15 is an experimental photograph in which the first heat treatment step is performed for 10 hours in the manufacturing method according to various embodiments of the present invention.

Meanwhile, in the present reaction, it is preferred to perform the heat treatment for 3 to 8 hours in the first heat treatment step (S105). FIG. 14 is an experimental photograph in which the first heat treatment step (S105) is performed for 4 hours in the manufacturing method according to various embodiments of the present invention, and as illustrated in FIG. 14, it can be confirmed that the substrate 107 and the solid electrolyte 103 are joined and sealed with each other. If the heat treatment time is less than 3 hours, there is a problem in that a chemical reaction between the substrate 107 and the solid electrolyte 103 does not sufficiently occur. FIG. 13 is an experimental photograph in which the first heat treatment step (S105) is performed for 2 hours in the manufacturing method according to various embodiments of the present invention, and as illustrated in FIG. 13, it can be confirmed that the substrate 107 and the solid electrolyte 103 are not sufficiently joined with each other. Further, when the heat treatment time is 8 hours or more, there is a problem in that the substrate 107 and the solid electrolyte 103 are overreacted. FIG. 15 is an experimental photograph in which the first heat treatment step (S105) is performed for 10 hours in the manufacturing method according to various embodiments of the present invention, and as illustrated in FIG. 15, it may be confirmed that the substrate 107 and the solid electrolyte 103 are overreacted.

Various embodiments of the present invention may be variously applied to the field which requires sealing at the boundary of heterogeneous materials, and has an advantage in that particularly in a solid electrolyte gas sensor requiring rigorous sealing, the performance of the sensor may be improved by perfectly sealing the boundary of heterogeneous materials through a reaction layer.

Figure 19:
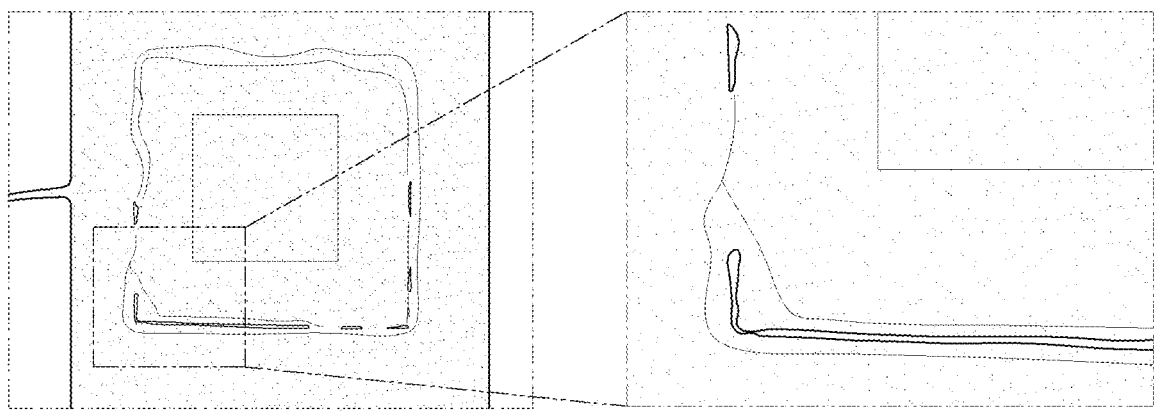
FIG. 19 is a photograph of a sealed part of a solid electrolyte $CO_2$ sensor according to the related art.
Figure 20:
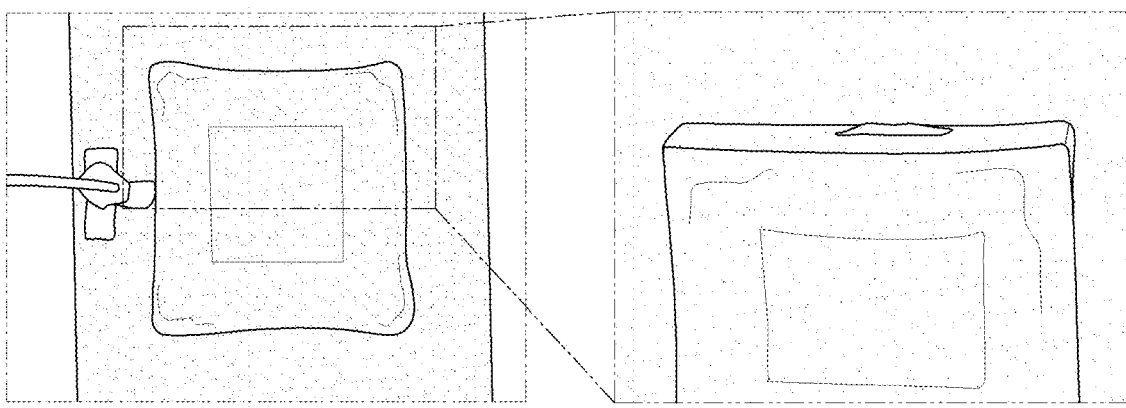
FIG. 20 is a photograph of a joining and sealing part of a solid electrolyte $CO_2$ sensor according to various embodiments of the present invention.

FIG. 19 is a photograph of a sealed part of a solid electrolyte $CO_2$ sensor according to the related art, and FIG. 20 is a photograph of a joining and sealing part of a solid electrolyte $CO_2$ sensor according to various embodiments of the present invention. In the related art, the substrate 7 and the solid electrolyte 3 are joined with each other by using a sealing material 9. However, since the thermal expansion coefficients of the substrate 7, the solid electrolyte 3, and the sealing material 9 are different from each other, the expansions are different from each other when the temperature is increased, so that there is a problem in that as illustrated in FIG. 19, cracks occur. However, in the present invention, the substrate 107 and the solid electrolyte 103 are joined and sealed with each other by a reaction caused by heat treatment while a new product is produced as illustrated in FIG. 20. For this reason, in the related art, other gases, particularly, moisture infiltrates through cracked chasms, and thus the reliability of the measurement of the concentration of carbon dioxide is reduced. However, the present invention has an advantage in that the substrate 107 and the solid electrolyte 103 are joined and sealed with each other by the reaction to produce no chasms, and thus, a gas, particularly, moisture fails to infiltrate, thereby increasing the reliability of the measurement of the concentration of carbon dioxide.

Figure 21:
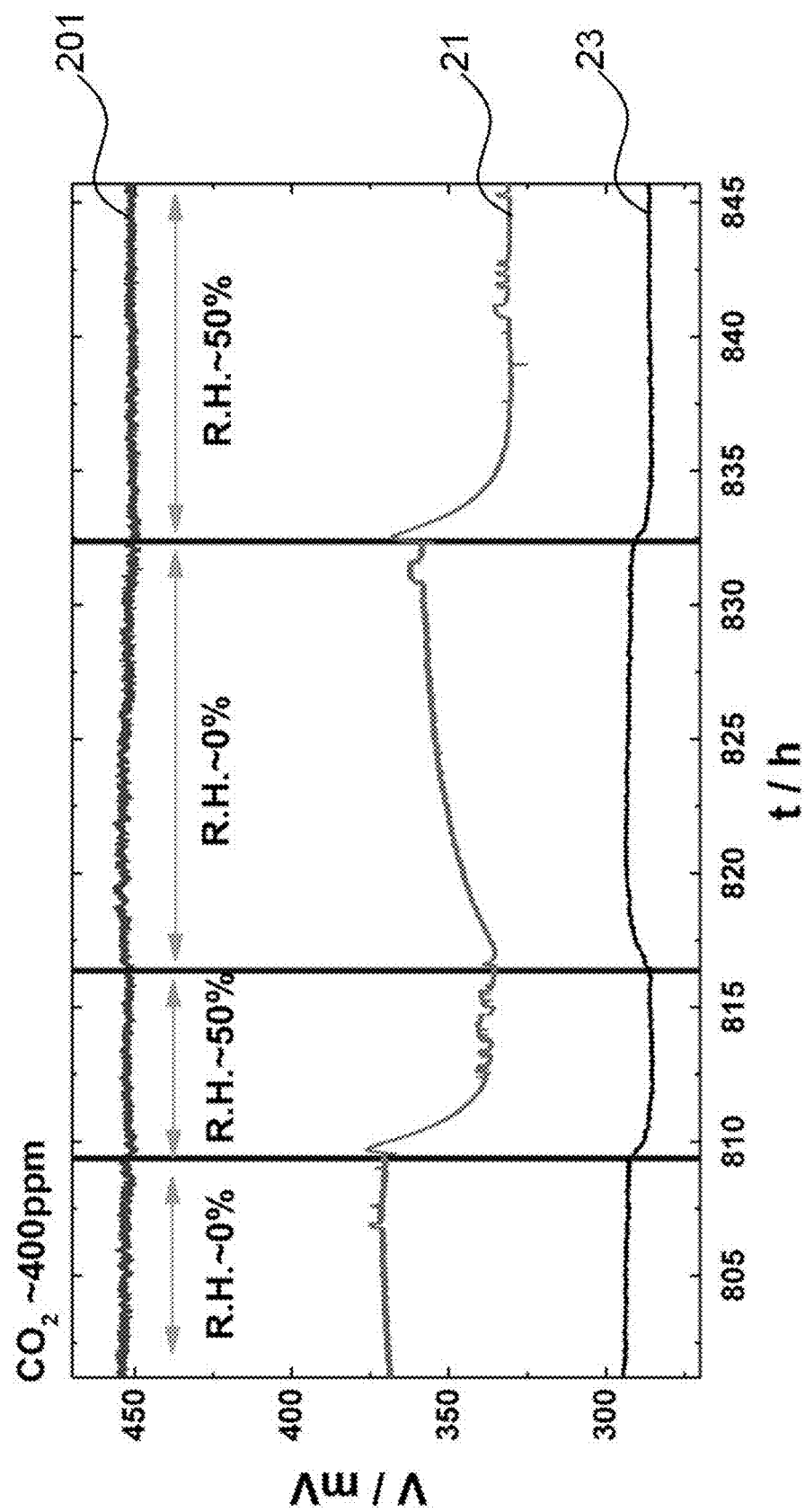
FIG. 21 is a moisture reaction experimental result graph of a solid electrolyte $CO_2$ sensor using a sintered body which is a solid electrolyte according various embodiments of the present invention and a solid electrolyte $CO_2$ sensor according to the related art.
Figure 22:
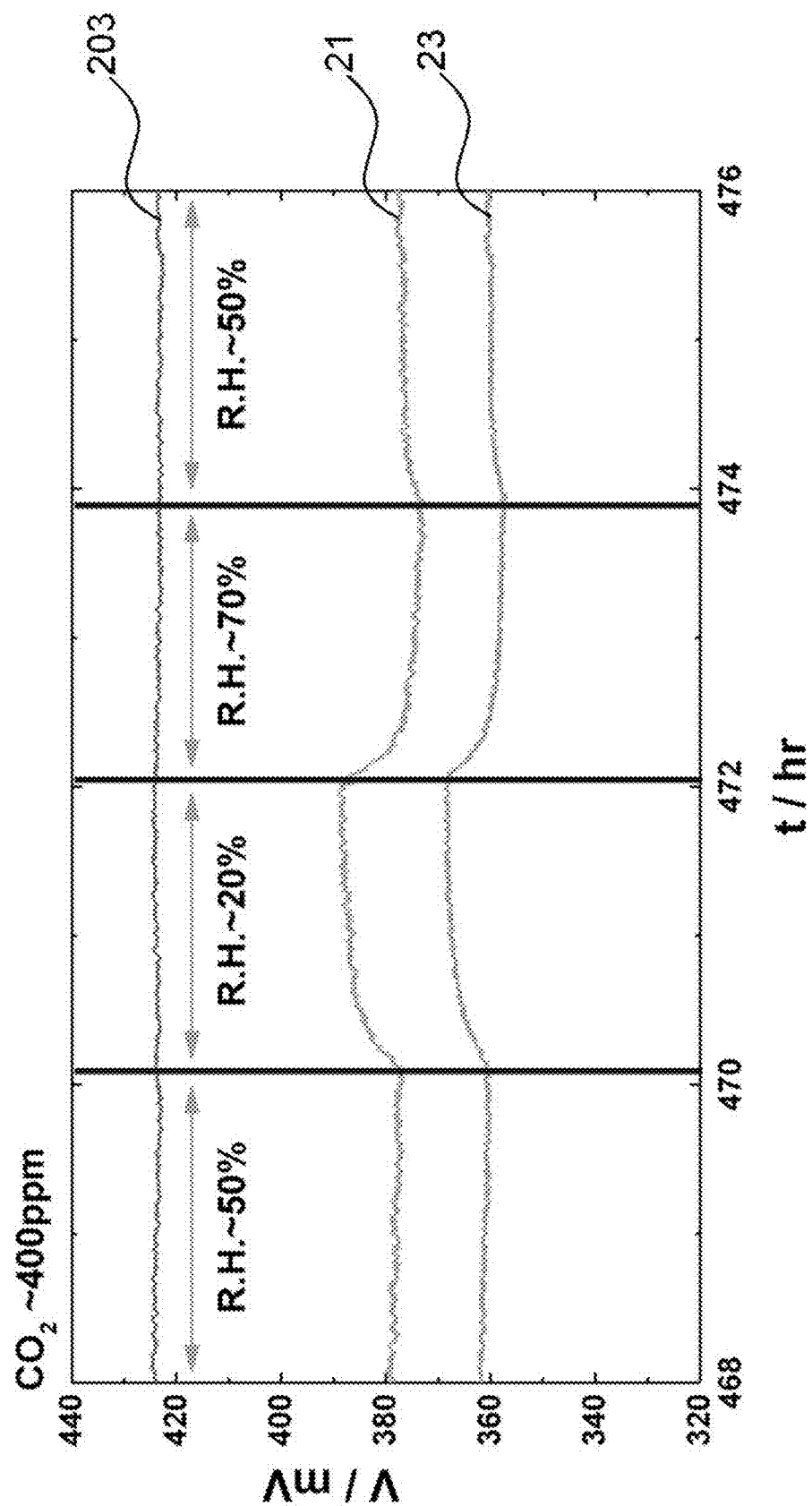
FIG. 22 is a moisture reaction experimental result graph of a solid electrolyte $CO_2$ sensor using a green sheet which is a solid electrolyte according to an exemplary embodiment of the present invention and a solid electrolyte $CO_2$ sensor according to the related art.

Additionally, experiments are performed on the moisture adsorption side reactions of various embodiments of the present invention and the related art while varying the relative humidity at a carbon dioxide concentration of 400 ppm. FIG. 21 is a moisture reaction experimental result graph of a solid electrolyte $CO_2$ sensor using a sintered body which is a solid electrolyte 103 according to various embodiments of the present invention and a solid electrolyte $CO_2$ sensor according to the related art. The horizontal axis is time, and the vertical axis is voltage. R.H. means the relative humidity. In FIG. 21, it can be confirmed that the curve 201 in the case where the solid electrolyte 103 is used as a sintered body exhibits a predetermined value even though the relative humidity is changed in the vicinity of 450 mV. However, it can be confirmed that the curve in the case of the related art, that is, the case of performing sealing by using the sealing material 9, that is, the curves 21, 23 of Comparative Example 1 and Comparative Example 2 vary depending on the relative humidity. FIG. 22 is a moisture reaction experimental result graph of a solid electrolyte $CO_2$ sensor using a green sheet which is a solid electrolyte according to various embodiments of the present invention and a solid electrolyte $CO_2$ sensor according to the related art. The horizontal axis is time, and the vertical axis is voltage. R.H. means the relative humidity. In FIG. 22, it can be confirmed that the curve 203 in the case where the solid electrolyte 103 is used as a green sheet exhibits a predetermined value even though the relative humidity is changed in the vicinity of 420 mV. However, it can be confirmed that the curve in the case of the related art, that is, the case of performing sealing by using the sealing material 9, that is, the curves 21, 23 of Comparative Example 1 and Comparative Example 2 vary depending on the relative humidity.

Various embodiments of the present invention have advantages in that the joining and sealing of the substrate and the solid electrolyte due to the reaction there between and completely blocking the reference electrode from the outside allow the reference electrode to suppress a side reaction with moisture, thereby improving the reliability of the measurement of the concentration of carbon dioxide and simplifying the manufacturing process to facilitate mass production. Furthermore, there are advantages in that the concentration of $CO_2$ in a vehicle while driving is monitored in real time to control the quality of automobile indoor air through the connection with the air conditioning system.

For convenience in explanation and accurate definition in the appended claims, the terms "upper" or "lower", "inner" or "outer" and etc. are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A solid electrolyte $CO_2$ sensor comprising:
   a sintered solid electrolyte;
   a sensing electrode formed at a first side of the solid electrolyte; and
   a reference electrode formed between a second side of the solid electrolyte and one surface of a sintered substrate,
   wherein the solid electrolyte has a larger area than the reference electrode,
   wherein a lateral side of the reference electrode is sealed by joining an end portion of the solid electrolyte to the substrate by a heat treatment, wherein the solid electrolyte is reacted with the substrate by the heat treatment, and
   wherein the solid electrolyte has a thickness of 200 to 400 μm.

2. The solid electrolyte $CO_2$ sensor of claim 1, wherein the reference electrode comprises at least one of a two phase mixture of Li(Na)—Ti(Fe)—O systems and Pt(Au).

3. The solid electrolyte $CO_2$ sensor of claim 1, wherein the sensing electrode is selected from the group consisting of $A_2CO_3$ (A=Li, Na), and a mixture of $A_2CO_3$ (A=Li, Na) and $BCO_3$ (B=Ba, Ca, Sr).

4. The solid electrolyte $CO_2$ sensor of claim 1, wherein the solid electrolyte comprises $Na_{1+x}Zr_2Si_xP_{3-x}O_{12}$, and $0<X<3$.

5. The solid electrolyte $CO_2$ sensor of claim 1, wherein the solid electrolyte comprises $Li_{2+2x}Zn_{1-x}GeO_4$, and $0<X<1$.

6. The solid electrolyte $CO_2$ sensor of claim 1, wherein an area of the solid electrolyte which is bonded to the substrate and does not join and seal the substrate comprises 20 to 90% of an area of the entire solid electrolyte.

7. The solid electrolyte $CO_2$ sensor of claim 1, wherein the substrate comprises alumina or mullite.

8. A method for manufacturing a solid electrolyte $CO_2$ sensor, the method comprising:
   stacking a reference electrode on a sintered substrate;
   stacking a sintered solid electrolyte having a thickness of 200 to 400 μm and a larger area than the reference electrode stacked on the substrate to stack an end portion of the solid electrolyte on the substrate;
   a first heat treatment, of subjecting the substrate, the reference electrode, and the solid electrolyte which are stacked to heat treatment to join the solid electrolyte to the substrate whereby a lateral side of the reference electrode is sealed; and seal the substrate, the reference electrode, and the solid electrolyte, wherein the solid electrolyte is reacted with the substrate by the heat treatment;
   stacking a sensing electrode on the stacked solid electrolyte; and
   a second heat treatment, of performing a heat treatment in order to bond the sensing electrode onto the solid electrolyte.

9. The method of claim 8, wherein the reference electrode comprises at least one of a two phase mixture of Li(Na)—Ti(Fe)—O systems and Pt(Au).

10. The method of claim 8, wherein the sensing electrode comprises at least one of $A_2CO_3$ (A=Li, Na) and a mixture of $A_2CO_3$ (A=Li, Na) and $BCO_3$ (B=Ba, Ca, Sr).

11. The method of claim 8, wherein the solid electrolyte comprises $Na_{1+x}Zr_2Si_xP_{3-x}O_{12}$, and $0<X<3$.

12. The method of claim 8, wherein the solid electrolyte comprises $Li_{2+2x}Zn_{1-x}GeO_4$ and $0<X<1$.

13. The method of claim 8, wherein in the stacking of the solid electrolyte, an area of the solid electrolyte which is bonded to the substrate and does not join and seal the substrate comprises 20 to 90% of an area of the entire solid electrolyte.

14. The method of claim 8, wherein the substrate comprises at least one of alumina and mullite.

15. The method of claim 8, wherein in the stacking of the solid electrolyte, a sintered body or a green sheet is used.

16. The method of claim 15, wherein when the first heat treatment uses a sintered body in the stacking of the solid electrolyte, a heat treatment for joining and sealing is performed in a temperature range which is 10 to 60° C. lower than a sintering temperature of the solid electrolyte.

17. The method of claim 15, wherein when the first heat treatment uses a green sheet in the stacking of the solid electrolyte, a heat treatment for joining and sealing is performed in a temperature range of a sintering temperature of the solid electrolyte to a temperature which is 50° C. lower than the sintering temperature of the solid electrolyte.

18. The method of claim 8, wherein the first heat treatment is performed for 3 to 8 hours in the first heat treatment.

* * * * *